United States Patent
Isler et al.

(10) Patent No.: US 7,067,549 B2
(45) Date of Patent: Jun. 27, 2006

(54) PYRROLIDONE CARBOXAMIDES

(75) Inventors: Markus Isler, Allschwil (CH); Thomas Giller, Wintersingen (CH); Günter Schwalm, Binningen (CH); Matthias Steger, Zürich (CH); Kurt Hilpert, Hofstetten (CH); Oliver Valdenaire, Allschwil (CH); Volker Breu, Schliengen (DE)

(73) Assignee: Actelion Pharmaceuticals AG, Allschwil (CH)

( * ) Notice: Subject to any disclaimer, the term of this patent is extended or adjusted under 35 U.S.C. 154(b) by 69 days.

(21) Appl. No.: 10/500,604

(22) PCT Filed: Dec. 27, 2002

(86) PCT No.: PCT/CH02/00725

§ 371 (c)(1), (2), (4) Date: Jun. 30, 2004

(87) PCT Pub. No.: WO03/059905

PCT Pub. Date: Jul. 24, 2003

(65) Prior Publication Data

US 2005/0192292 A1 Sep. 1, 2005

(30) Foreign Application Priority Data

Dec. 31, 2001 (CH) .................... 2381/01

(51) Int. Cl.
*A61K 31/403* (2006.01)
*C07D 209/82* (2006.01)

(52) U.S. Cl. .................... 514/411; 548/440

(58) Field of Classification Search ........... 548/440; 514/411
See application file for complete search history.

(56) References Cited

U.S. PATENT DOCUMENTS 5,281,612 A  1/1994  Domagala et al.
6,166,015 A * 12/2000  Rogers et al. ............ 514/243

FOREIGN PATENT DOCUMENTS

| EP | 0 393 607 A | 10/1990 |
|---|---|---|
| GB | 856 452 A | 12/1960 |
| GB | 2 351 733 A | 1/2001 |
| WO | WO 01/07409 * | 2/2001 |
| WO | WO 01/85714 | 11/2001 |

* cited by examiner

*Primary Examiner*—Golam M. M. Shameem
*Assistant Examiner*—Andrew B. Freistein
(74) *Attorney, Agent, or Firm*—Hoffmann & Baron, LLP

(57) ABSTRACT

Pyrrolidone carboxamides of formula (I) where $R^2$=a group of formula (a) or (b), $R^5$=phenyl, heteroalkyl, aryloxy, alkoxy, alkanoyl or —$NR^6R^7$ and $R^1$, X, $R^3$, $R^4$, $R^6$ and $R^7$ have the meanings given in the description and the claims, pharmaceutically applicable acid addition salts with basic compounds of formula (I), pharmaceutically applicable salts of acid compounds of formula (I) with bases, pharmaceutically applicable esters of hydroxy- or carboxy-group containing compounds of formula (I) and hydrates and solvates thereof, inhibit the interaction of neuropeptide Y (NPY) with one of the neuropeptide receptor subtypes (NPY-Y5) and are particularly suitable for the prevention and treatment of arthritis, diabetes and especially eating disorders and obesity. The above can be produced by known methods and converted into a galenic dosage form.

9 Claims, No Drawings

PYRROLIDONE CARBOXAMIDES

CROSS-REFERENCE TO RELATED APPLICATIONS

This application is the National Stage of International Application No. PCT/CH02/00725, filed Dec. 27, 2002, which claimed the benefit of Switzerland Application No. 2381/01, filed Dec. 31, 2001 and PCT/CH02/00429, filed Aug. 5, 2002, the contents of which are incorporated by reference herein.

FIELD OF THE INVENTION

The present invention relates to pyrrolidonecarboxamide derivatives.

BACKGROUND OF THE INVENTION

WO 01/074090 A1 relates to carbazole derivatives whose general formula partially overlaps with the below formula I but does not specifically describe a single compound covered by the below formula I and, furthermore, does not contain any sufficient concrete general pointers in the direction of compounds of the below formula I.

SUMMARY OF THE INVENTION

In particular, the invention relates to pyrrolidone-carboxamides of the formula

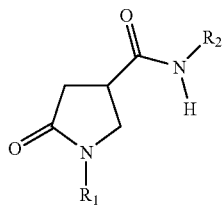

I in which
$R^1$ is phenyl which is optionally monosubstituted or disubstituted in the phenyl radical by alkyl, alkoxy, dialkylamino, halogen or trifluoromethyl, benzyl, phenylethyl or α-hydroxyphenylethyl; naphthyl or naphthylmethyl; thienyl-, furyl-, pyridyl-, 1-alkylpyrrolidin-2-yl-, pyrrolidino- or morpholino-alkyl; or cycloalkyl which can optionally possess a fused-on benzene ring;
$R^2$ is a radical of the formula

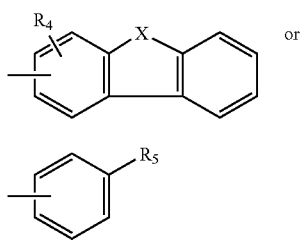

X is —CH$_2$—, —CO—, —O— or —NR$^3$—;
$R^3$ is hydrogen or alkyl;
$R^4$ is hydrogen or alkoxy;

$R^5$ is phenyl, heteroalkyl, aryloxy, alkoxy, alkanoyl or —NR$^6$R$^7$;
$R^6$ is hydrogen, alkyl, aralkyl, cycloalkylalkyl or alkoxycarbonylalkyl; and
$R^7$ is aryl, heteroaryl, alkyl, hydroxyalkyl or acyl;

to pharmaceutically utilizable acid addition salts of basic compounds of the formula I, to pharmaceutically utilizable salts of acid compounds of the formula I with bases, to pharmaceutically utilizable esters of compounds of the formula I which contain hydroxyl or carboxyl groups, and to hydrates or solvates thereof.

Since the pyrrolidonecarboxamides of the formula I contain at least one asymmetric C atom, they can be present as optically pure enantiomers, as mixtures of enantiomers, such as racemates, or, where appropriate, as optically pure diastereomers, as mixtures of diastereomers, as diastereomeric racemates or as mixtures of diastereomeric racemates.

The compounds defined at the outset are novel and are distinguished by possessing valuable pharmacodynamic properties. They inhibit the interaction of the neuro-peptide Y (NPY) with one of the neuropeptide receptor subtypes (NPY-Y5) and are suitable, in particular, for preventing and treating arthritis, diabetes and, especially, eating disturbances and obesity.

The present invention relates to the above compounds as such and as therapeutic active compounds; to processes and intermediates for preparing them; to pharmaceuticals which comprise one of the above compounds; and to the use of the above compounds for preventing and treating arthritis, diabetes and, especially, eating disturbances and obesity or for producing corresponding pharmaceuticals.

DETAILED DESCRIPTION OF PREFERRED EMBODIMENTS

In the present description, the term "alkyl" denotes, on its own or in combination, a branched or unbranched saturated hydrocarbon radical having from 1 to 8 carbon atoms, preferably having from 1 to 6 carbon atoms and, particularly preferably, having from 1 to 4 carbon atoms. Examples of these radicals are methyl, ethyl, n-propyl, isopropyl, n-butyl, isobutyl, sec-butyl, tert-butyl, the isomeric pentyls, the isomeric hexyls and the isomeric octyls; methyl, ethyl, n-propyl, isopropyl, n-butyl, isobutyl and the like are preferred.

The term "cycloalkyl" denotes, on its own or in combination, a saturated cyclic hydrocarbon radical having 3–8 carbon atoms, preferably having from 3 to 6 carbon atoms, which can be substituted, for example by alkyl groups, such as methyl, and which can possess a fused-on benzene ring. Examples of cycloalkyl groups which are optionally substituted by alkyl are cyclopropyl, methylcyclopropyl, dimethylcyclopropyl, cyclobutyl, methylcyclobutyl, cyclopentyl, methylcyclopentyl, cyclohexyl, methylcyclohexyl, dimethylcyclohexyl, cycloheptyl and cyclooctyl; examples of cycloalkyl radicals having a fused-on benzene ring are 1-indanyl, 2-indanyl and the like.

The term "hydroxyalkyl" denotes, on its own or in combination, an alkyl group, as described above, with one or two H atoms, preferably one H atom, being replaced with a hydroxyl group. Examples are hydroxymethyl, hydroxyethyl, hydroxypropyl and the like.

The term "alkoxy" denotes, on its own or in combination, an alkyl radical, as described above, which is linked by way of an oxygen bridge. Examples are methoxy, ethoxy and the like.

The term "alkanoyl" denotes, on its own or in combination, an alkyl group, as described above, which is linked by way of a CO bridge. Examples are acetyl, 3-methylbutyryl, 2,2-dimethylpropionyl and the like.

The term "aryl" denotes, on its own or in combination, a phenyl or naphthyl group, preferably a phenyl group, which can carry up to four, preferably from one to three and particularly preferably one or two, substituents. Examples of such substituents are alkyl, hydroxyalkyl, alkoxy, alkoxyalkyl, nitro, fluoro, bromo, chloro, hydroxy, dialkylamino and the like. Particularly preferred substituents are alkyl and alkoxy. Examples of these aryl groups are phenyl, methylphenyl, dimethylphenyl, ethylphenyl, isopropylphenyl, methoxyphenyl, methoxymethylphenyl, dimethylaminophenyl, phenylaminophenyl and the like.

The term "aralkyl" denotes, on its own or in combination, an alkyl group, as described above, in which at least one H atom is replaced with an aryl group, as described above, in particular with a phenyl or naphthyl group, which can carry one or more substituents, such as alkyl or alkoxy groups. Examples of these aralkyl radicals are benzyl, phenethyl, 2-(3,4-dimethoxyphenyl)ethyl and the like.

The term "heteroaryl" denotes, on its own or in combination, an aromatic monocyclic, bicyclic or tricyclic heterocyclic ring system having from 5 to 10, preferably from 5 to 6, ring members which contains from one to four, preferably from one to two, heteroatoms which are selected, independently of one another, from nitrogen, oxygen and sulphur. Examples of these heteroaryl groups are pyridyl, pyrimidinyl, thiazolyl, thiophenyl, furanyl, tetrazolyl, carbazolyl and the like. These heteroaryl groups can be substituted, expediently monosubstituted, disubstituted or trisubstituted, with suitable substituents primarily being alkyl, alkoxy, amino or aryl groups. Examples are 2-pyridyl, 2-thienyl, 4,6-dimethyl-2-pyrimidinyl and the like.

The term "acyl" denotes, alone or in combination, an alkanoyl group, as described above, or a cycloalkyl, aryl, aralkyl or heteroaryl group, as described above, which is linked by way of a CO bridge. Examples are, as mentioned above, acetyl, 3-methylbutyryl and 2,2-dimethylpropionyl as well as cyclopropanecarbonyl, benzoyl, phenylacetyl, 2-methoxybenzoyl, 4-methoxybenzoyl, 3-fluorobenzoyl, benzo[1,3]dioxole-5-carbonyl, furan-2-carbonyl and the like.

The term "pharmaceutically utilizable salts" relates to those salts which do not impair the biological effect and properties of the free bases or free acids and which are not undesirable biologically or in some other way. The salts are formed from the free bases using inorganic acids, such as hydrochloric acid, hydrobromic acid, sulfuric acid, nitric acid, phosphoric acid and the like, preferably hydrochloric acid, or using organic acids, such as acetic acid, propionic acid, glycolic acid, pyruvic acid, oxalic acid, maleic acid, malonic acid, succinic acid, tartaric acid, salicylic acid, citric acid, benzoic acid, mandelic acid, methanesulfonic acid, p-toluenesulfonic acid and the like. The free acids can form salts with inorganic bases or with organic bases. Preferred salts with inorganic bases are, but not exclusively, sodium salts, potassium salts, lithium salts, ammonium salts, calcium salts, magnesium salts and the like. Preferred salts with organic bases are, but not exclusively, salts with primary, secondary and tertiary amines, substituted amines, including all naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like. Compounds of formula I can also be present as zwitterions.

The invention also includes pharmaceutically suitable esters of compounds of the formula I which contain hydroxyl or carboxyl groups. "Pharmaceutically suitable esters" means that, in compounds of the formula I, corresponding functional groups are derivatized to form ester groups such that they are once again retransformed, in vivo, into their active form. On the one hand, COOH groups can be esterified. Examples of suitable esters of this nature are the alkyl esters and aralkyl esters. Preferred esters of this nature are the methyl, ethyl, propyl, butyl and benzyl esters as well as the (R/S)-1-[(isopropoxycarbonyl)oxy]ethyl esters. The ethyl esters and the isomeric butyl esters are particularly preferred. On the other hand, OH groups can be esterified. Examples of these compounds contain physiologically acceptable and metabolically labile ester groups, such as methoxymethyl ester, methylthiomethyl ester and pivaloyloxymethyl ester, and similar ester groups.

Preferred possible meanings for $R^1$ are phenyl, 4-tolyl, 2,5-dimethylphenyl, 2-isopropylphenyl, 3-methoxyphenyl, 2-methyl-5-methoxyphenyl, benzyl, 2-phenylethyl, 2-(2-pyridyl)ethyl, 2-(2-thienyl)ethyl, 2-indanyl and 2-morpholinoethyl. Other preferred possible meanings for $R^1$ are cycloheptyl, 2-hydroxy-2-phenylethyl, 2-thienylmethyl, 2-furanylmethyl, 4-chlorobenzyl, 3-fluorophenyl, 2-chlorobenzyl and 2,4-dimethoxybenzyl as well as 2-naphthyl, naphthalen-1-ylmethyl, 4-dimethylaminophenyl, 2-pyrrolidin-1-ylethyl, 1-methylpyrrolidin-2-ylethyl, 4-isopropylphenyl and 3,5-bis-trifluoromethylphenyl.

Particularly preferred possible meanings for $R^1$ are 2,5-dimethylphenyl, 2-isopropylphenyl and 2-methyl-5-methoxyphenyl.

Preferred possible meanings for $R^2$ are biphenyl-4-yl, 4-methoxyphenyl, 4-phenoxyphenyl, 4-dimethylaminophenyl, 4-diethylaminophenyl, 4-phenylaminophenyl, 4-[N-ethyl-N-(2-hydroxyethyl)amino]phenyl, 4-(N-ethyl-N-isopropylamino)phenyl, 4-N-(4,6-dimethyl-2-pyrimidinyl)aminophenyl, 4-[N-ethyl-N-(4,6-dimethyl-2-pyrimidinyl)amino]phenyl, 4-[N-methyl-N-(4,6-dimethyl-2-pyrimidinyl)amino]phenyl, 4-acetylphenyl, 9H-fluoren-2-yl, 9-oxo-9H-fluoren-2-yl and 9-ethylcarbazol-3-yl. Other preferred possible meanings for $R^2$ are 4-(N-ethoxycarbonylmethyl-N-phenylamino)phenyl, 4-(N-ethyl-N-phenylamino)phenyl, 4-(N-methyl-N-phenylaminophenyl, 4-(N-cyclopropylmethyl-N-phenylamino)phenyl, 4-(N-isobutyl-N-phenylamino)phenyl, 4-(2-methoxybenzoylamino)phenyl, 4-(2,2-dimethylpropionylamino)phenyl, 4-(3-methylbutyrylamino)phenyl, 4-(cyclopropanecarbonylamino)phenyl, 4-(3-fluorobenzoylamino)phenyl and 4-[(furan-2-carbonyl)amino]phenyl as well as biphenyl-3-yl, 9H-fluoren-1-yl, 2-methoxydibenzofuran-3-yl, 4-(N-isopropyl-N-phenylamino)phenyl, 4-(N-benzyl-N-phenylamino)phenyl, 4-acetylaminophenyl, 4-benzoylaminophenyl, 4-phenylacetylaminophenyl, 4-[(benzo[1,3]dioxole-5-carbonyl)amino]phenyl and 4-(4-methoxybenzoylamino)phenyl.

Particularly preferred possible meanings of $R^2$ are 9-ethyl-9H-carbazol-3-yl, 4-[N-ethyl-N-(4,6-dimethyl-2-pyrimidinyl)amino]phenyl, 4-[N-methyl-N-(4,6-dimethyl-2-pyrimidinyl)amino]phenyl, 4-(4,6-dimethyl-2-pyrimidinyl)amino]phenyl, 4-phenylaminophenyl, 4-diethylaminophenyl, 4-(N-ethyl-N-isopropylamino)phenyl, 4-(N-ethoxycarbonylmethyl-N-phenylamino)phenyl, 4-(N-ethyl-N-phenylamino)phenyl, 4-(N-methyl-N-phenylamino)phenyl and 2,4-dimethoxybenzyl.

Representative examples of preferred compounds of formula I are:

rac. N-(9-Ethyl-9H-carbazol-3-yl)-5-oxo-1-(2-pyridin-2-ylethyl)pyrrolidine-3-carboxamide;

rac. N-(9-Ethyl-9H-carbazol-3-yl)-1-(2-hydroxy-2-phenylethyl)-5-oxopyrrolidine-3-carboxamide;

rac. N-(4-Diethylaminophenyl)-1-(2,5-dimethylphenyl)-5-oxopyrrolidine-3-carboxamide;

rac. N-(9-Ethyl-9H-carbazol-3-yl)-5-oxo-1-(2-thiophen-2-ylethyl)pyrrolidine-3-carboxamide;

rac. N-(9-Ethyl-9H-carbazol-3-yl)-1-(4-chlorobenzyl)-5-oxopyrrolidine-3-carboxamide;

rac. N-(9-Ethyl-9H-carbazol-3-yl)-5-oxo-1-thiophen-2-ylmethylpyrrolidine-3-carboxamide;

rac. N-(9-Ethyl-9H-carbazol-3-yl)-1-furan-2-ylmethyl-5-oxopyrrolidine-3-carboxamide;

rac. N-(9-Ethyl-9H-carbazol-3-yl)-1-(2-isopropylphenyl)-5-oxopyrrolidine-3-carboxamide;

rac. N-(9-Ethyl-9H-carbazol-3-yl)-1-(5-methoxy-2-methylphenyl)-5-oxopyrrolidine-3-carboxamide;

rac. N-[4-(Ethylisopropylamino)phenyl]-1-(2,5-dimethylphenyl)-5-oxopyrrolidine-3-carboxamide;

rac. N-(9-Ethyl-9H-carbazol-3-yl)-5-oxo-1-phenethylpyrrolidine-3-carboxamide;

rac. Ethyl [(4-{[1-(2,5-dimethylphenyl)-5-oxopyrrolidine-3-carbonyl]amino}phenyl)phenylamino]acetate;

rac. N-(9-Ethyl-9H-carbazol-3-yl)-1-cycloheptyl-5-oxopyrrolidine-3-carboxamide;

rac. N-{4-[(4,6-Dimethylpyrimidin-2-yl)ethylamino]phenyl}-1-(5-methoxy-2-methylphenyl)-5-oxopyrrolidine-3-carboxamide;

rac. N-{4-[Ethyl-(2-hydroxyethyl)amino]phenyl}-1-(2,5-dimethylphenyl)-5-oxopyrrolidine-3-carboxamide;

rac. N-[4-(Ethylphenylamino)phenyl]-1-(2,5-dimethylphenyl)-5-oxopyrrolidine-3-carboxamide;

rac. N-(9-Ethyl-9H-carbazol-3-yl)-1-(3-methoxyphenyl)-5-oxopyrrolidine-3-carboxamide;

rac. N-(9-Ethyl-9H-carbazol-3-yl)-1-(2-chlorobenzyl)-5-oxopyrrolidine-3-carboxamide;

rac. N-[4-(4,6-Dimethylpyrimidin-2-ylamino)phenyl]-1-(2,5-dimethylphenyl)-5-oxopyrrolidine-3-carboxamide;

rac. N-{4-[(4,6-Dimethylpyrimidin-2-yl)methylamino]phenyl}-1-(2,5-dimethylphenyl)-5-oxopyrrolidine-3-carboxamide;

rac. N-(9-Ethyl-9H-carbazol-3-yl)-5-oxo-1-phenylpyrrolidine-3-carboxamide;

rac. N-{4-[(4,6-Dimethylpyrimidin-2-yl)methylamino]phenyl}-5-oxo-1-p-tolylpyrrolidine-3-carboxamide;

rac. N-[4-(Isopropylphenylamino)phenyl]-1-(2,5-dimethylphenyl)-5-oxopyrrolidine-3-carboxamide;

rac. N-[4-(Ethylphenylamino)phenyl]-1-(2-isopropylphenyl)-5-oxopyrrolidine-3-carboxamide;

rac. N-{4-[(4,6-Dimethylpyrimidin-2-yl)ethylamino]phenyl}-5-oxo-1-(2-pyridin-2-ylethyl)pyrrolidine-3-carboxamide;

rac. N-[4-(4,6-Dimethylpyrimidin-2-ylamino)phenyl]-1-(2-isopropylphenyl)-5-oxopyrrolidine-3-carboxamide;

rac. N-[4-(4,6-Dimethylpyrimidin-2-ylamino)phenyl]-1-(5-methoxy-2-methylphenyl)-5-oxopyrrolidine-3-carboxamide;

rac. N-[4-(Methylphenylamino)phenyl]-1-(2,5-dimethylphenyl)-5-oxopyrrolidine-3-carboxamide;

rac. N-[4-(Methylphenylamino)phenyl]-1-(2-isopropylphenyl)-5-oxopyrrolidine-3-carboxamide;

rac. N-(9-Ethyl-9H-carbazol-3-yl)-1-(4-isopropylphenyl)-5-oxopyrrolidine-3-carboxamide;

rac. N-(9-Ethyl-9H-carbazol-3-yl)-1-(3-fluorophenyl)-5-oxopyrrolidine-3-carboxamide;

rac. N-(4-Phenylaminophenyl)-1-(2,5-dimethylphenyl)-5-oxopyrrolidine-3-carboxamide;

rac. N-[4-(4,6-Dimethylpyrimidin-2-ylamino)phenyl]-1-indan-2-yl-5-oxopyrrolidine-3-carboxamide;

rac. N-[4-(Ethylphenylamino)phenyl]-1-(5-methoxy-2-methylphenyl)-5-oxopyrrolidine-3-carboxamide;

rac. N-{4-[(4,6-Dimethylpyrimidin-2-yl)methylamino]phenyl}-1-(2-isopropylphenyl)-5-oxopyrrolidine-3-carboxamide;

rac. N-(9-Ethyl-9H-carbazol-3-yl)-1-benzyl-5-oxopyrrolidine-3-carboxamide;

rac. N-[4-(4,6-Dimethylpyrimidin-2-ylamino)phenyl]-5-oxo-1-p-tolylpyrrolidine-3-carboxamide;

rac. N-(9-Ethyl-9H-carbazol-3-yl)-1-indan-2-yl-5oxopyrrolidine-3-carboxamide;

rac. N-{4-[(4,6-Dimethylpyrimidin-2-yl)ethylamino]-phenyl}-1-(2-hydroxy-2-phenylethyl)-5-oxo-pyrrolidine-3-carboxamide;

rac. N-(Biphenyl-4-yl)-1-(2,5-dimethylphenyl)-5-oxopyrrolidine-3-carboxamide;

rac. N-[4-(Cyclopropylmethylphenylamino)phenyl]-1-(5-methoxy-2-methylphenyl)-5-oxopyrrolidine-3-carboxamide;

rac. N-[4-(Isopropylphenylamino)phenyl]-1-(2-isopropylphenyl)-5-oxopyrrolidine-3-carboxamide;

rac. N-(4-Phenylaminophenyl)-1-(2-isopropylphenyl)-5-oxopyrrolidine-3-carboxamide;

rac. N-{4-[(4,6-Dimethylpyrimidin-2-yl)methylamino]phenyl}-1-(5-methoxy-2-methylphenyl)-5-oxopyrrolidine-3-carboxamide;

rac. N-{4-[(4,6-Dimethylpyrimidin-2-yl)ethylamino]phenyl)-1-(3-methoxyphenyl)-5-oxopyrrolidine-3-carboxamide;

rac. N-{4-[(4,6-Dimethylpyrimidin-2-yl)methylamino]phenyl}-5-oxo-1-m-tolylpyrrolidine-3-carboxamide;

rac. N-[4-(Cyclopropylmethylphenylamino)phenyl]-1-(2,5-dimethylphenyl)-5-oxopyrrolidine-3-carboxamide;

rac. N-{4-[(4,6-Dimethylpyrimidin-2-yl)ethylamino]phenyl}-1-(2-isopropylphenyl)-5-oxopyrrolidine-3-carboxamide;

rac. Ethyl [(4-([1-(5-methoxy-2-methylphenyl)-5-oxopyrrolidine-3-carbonyl]amino}phenyl)phenylamino]acetate;

rac. N-[4-(Cyclopropylmethylphenylamino)phenyl]-1-(2-isopropylphenyl)-5-oxopyrrolidine-3-carboxamide;

rac. N-[4-(Ethylphenylamino)phenyl]-1-indan-2-yl-5-oxopyrrolidine-3-carboxamide; and rac. N-[4-(Isobutylphenylamino)phenyl]-1-(2-isopropylphenyl)-5-oxopyrrolidine-3-carboxamide.

Other representative examples of preferred compounds of formula I are:

rac. N-[4-(2-Methoxybenzoylamino)phenyl]-1-(2,5-dimethylphenyl)-5-oxopyrrolidine-3-carboxamide;

rac. N-[4-(2,2-Dimethylpropionylamino)phenyl]-1-(2,5-dimethylphenyl)-5-oxopyrrolidine-3-carboxamide;

rac. N-(9-Ethyl-9H-carbazol-3-yl)-1-(2-morpholin-4-ylethyl)-5-oxopyrrolidine-3-carboxamide;

rac. N-(9-Ethyl-9H-carbazol-3-yl)-5-oxo-1-p-tolylpyrrolidine-3-carboxamide; and rac. N-(9-Ethyl-9H-carbazol-3-yl)-1-(2,4-dimethoxybenzyl)-5-oxopyrrolidine-3-carboxamide; as well as rac. N-[4-(4,6-Dimethylpyrimidin-2-ylamino)phenyl]-1-(4-dimethylaminophenyl)-5-oxopyrrolidine-3-carboxamide; and rac. N-[4-(4,6-Dimethylpyrimidin-2-yl)methylamino-phenyl]-1-(4-dimethylaminophenyl)-5-oxopyrrolidine-3-carboxamide.

Compounds of the formula I can be prepared, according to the invention, by reacting a pyrrolidonecarboxylic acid of the formula III (see scheme below), in which $R^1$ has the meaning mentioned at the outset, or a reactive derivative thereof, with an amine of the formula IV, in which $R^2$ has the meaning mentioned at the outset, or a reactive derivative thereof. Any stereoisomeric mixtures, such as racemates, which are obtained can, if desired, be resolved using generally customary methods.

In order to prepare the corresponding pyrrolidone carboxylic acid of the formula III, it is possible, for example, to take the following route, with the substituents and indices given in the following scheme having the meanings mentioned at the outset unless otherwise indicated; this route consists in reacting an amine of the formula II, such as aniline or the like, in a solvent, such as water, dioxane, ethanol or the like, at elevated temperature, with itaconic acid (Buzas et al., Chim Ther 7, 398–403, 1972).

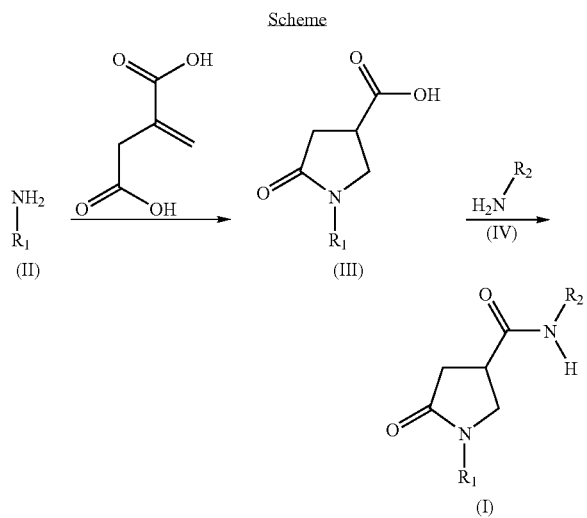

Scheme

The compounds of the formula I can be prepared by reacting a pyrrolidonecarboxylic acid of the formula III with an amine of the formula IV. For this, the pyrrolidonecarboxylic acid of the formula III is expediently converted, where appropriate in a suitable solvent, such as toluene, into the corresponding acid chloride using a halogenating agent such as $SOCl_2$ or $POCl_3$. This reactive derivative of the pyrrolidonecarboxylic acid of the formula III is then reacted with an amine of the formula IV in a suitable solvent, such as methylene chloride, in the presence of a base, such as triethylamine.

In a process variant, the pyrrolidonecarboxylic acid of the formula III is reacted with an amine of the formula IV in the added presence of a coupling reagent, such as EDC, DCC or BOP, in a solvent, such as DMF, and, where appropriate, in the presence of a base, such as triethylamine.

Compounds of the formula I in which $R^2$ is a radical of the formula (b), $R^5$ is $-NR^6R^7$ and $R^7$ is acyl can also be prepared by acylating a corresponding compound in which $R^7$ is hydrogen, such as rac. N-(4-aminophenyl)-1-(2,5-dimethylphenyl)-5-oxopyrrolidine-3-carboxamide, for example using acetyl chloride, isovaleryl chloride, cyclopropylcarbonyl chloride, benzoyl chloride, phenylacetyl chloride, 2-methoxybenzoyl chloride, piperonyloyl chloride, pivaloyl chloride, 4-methoxybenzoyl chloride, 3-fluorobenzoyl chloride and the like.

While only some of the pyrrolidonecarboxylic acids of the formula III are known, they can be prepared by methods which are known per se and with which every skilled person is familiar, for example using the abovementioned method (Buzas et al., Chim Ther 7, 398–403, 1972); furthermore, some of the examples which follow contain information regarding the preparation of particular pyrrolidonecarboxylic acids of the formula III.

Some of the amines of the formula IV are also known or can be prepared by methods which are known per se; some of the examples which follow also contain information regarding the preparation of particular amines of the formula IV.

Insofar as the starting compounds of the formulae III and IV, and also the nitro precursors of the compounds of the formula IV, are novel, they also form part of the subject matter of the present invention. Thus, the following compounds of the formula IV and their nitroprecursors, in particular:

ethyl [(4-nitrophenyl)phenylamino]acetate;
ethyl [(4-aminophenyl)phenylamino]acetate;
cyclopropylmethyl(4-nitrophenyl)phenylamine;
N-cyclopropylmethyl-N-phenylphenylene-1,4-diamine;
isobutyl(4-nitrophenyl)phenylamine;
N-isobutyl-N-phenylphenylene-1,4-diamine;
ethyl [(4-nitrophenyl)phenylamino]pentanoate;
ethyl [(4-aminophenyl)phenylamino]pentanoate;
benzyl(4-nitrophenyl)phenylamine; and
N-benzyl-N-phenylphenylene-1,4-diamine;

as well as the following compounds of the formula III:
rac. 1-indan-2-yl-5-oxopyrrolidine-3-carboxylic acid;
rac. 1-naphthalen-2-yl-5-oxopyrrolidine-3-carboxylic acid;
rac. 1-(5-methoxy-2-methylphenyl)-5-oxopyrrolidine-3-carboxylic acid;
rac. 5-oxo-1-(2-pyridin-2-ylethyl)pyrrolidine-3-carboxylic acid;
rac. 1-cycloheptyl-5-oxopyrrolidine-3-carboxylic acid;
rac. 1-(2-hydroxy-2-phenylethyl)-5-oxopyrrolidine-3-carboxylic acid;
rac. 5-oxo-1-(2-pyrrolidin-1-ylethyl)pyrrolidine-3-carboxylic acid;
rac. 1-[2-(1-methylpyrrolidin-2-yl)ethyl]-5-oxopyrrolidine-3-carboxylic acid; and
rac. 1-(3-fluorophenyl)-5-oxopyrrolidine-3-carboxylic acid;

are part of the subject matter of the present invention.

As mentioned at the outset, the compounds of the formula I and their pharmaceutically utilizable salts and esters are novel and possess valuable pharmacological properties. In particular, they inhibit the interaction of the neuropeptide Y (NPY) with one of the neuropeptide receptor subtypes (NPY-Y5). NPY is a regulatory, 36-amino acid peptide belonging to the pancreatic polypeptide family. NPY is the most widespread neuropeptide in the central and peripheral nervous systems and has prominent and complex effects on nutrient uptake, anxiety, depression, circadian rhythm, sexual function, reproduction, memory function, migraine, pain, epileptic seizures, blood pressure, cerebral hemorrhages, shock, sleep disturbance, diarrhea, etc.

NPY interacts with a heterogeneous population of at least five NPY receptor subtypes, i.e. Y1–Y5, which activate adenylate cyclase using a G protein. One of the most prominent effects is the induction of nutrient uptake in vertebrates. Recent investigations involving the selective activation and blocking of the individual NPY receptors have shown that it is principally the NPY-Y5 receptor which is responsible for appetite-inducing signals.

Obesity is an important and increasing problem in the industrialized world. Obesity is associated with a variety of diseases such as non-insulin-dependent diabetes (type II diabetes), high blood pressure, coronary diseases of the heart, dyslipidemia etc., and has an influence on the life expectancy and quality of life of the population affected. For this reason, there is a need for pharmaceutical substances which exert an influence on eating habits. The NPY-Y5 receptor is a possible target for a corresponding pharmacological intervention. Using a low molecular weight compound to inhibit this receptor represents an attractive possibility for preventing or treating the above diseases.

Because of their property of inhibiting the interaction of neuropeptide Y with the neuropeptide Y5 receptor subtype, the compounds of the formula I, and their pharmaceutically utilizable salts and esters, are suitable for preventing and treating arthritis, diabetes and, in particular, eating disturbances and obesity.

The valuable pharmacodynamic properties of the novel compounds according to the invention can be demonstrated using the methods which are described below.

Cloning the Mouse NPY-Y5 Receptor cDNAs

The full-length cDNA which contains the mouse NPY-Y5 (mNPY-Y5) receptor coding was amplified from mouse brain cDNA using specific primers, which were custom-made on the basis of published sequences, and employing Pfu DNA polymerase (Stratagene). The amplification product was subcloned into a mammalian expression vector pcDNA3 using EcoRI and XhoI restriction sites. Positive clones were sequenced; one clone, which contained the published sequence, was selected for preparing stable cell clones.

Stable Transfection

Human embryonic kidney 293 (HEK293) cells were transfected with 10 μg of mNPY5 DNA using Lipofectamine reagent (Gibco BRL) in accordance with the manufacturer's instructions. Two days after the transfection, the geneticin selection (1 mg/ml) was initiated and several stable clones were isolated. One of the clones was used for further pharmacological characterization.

Radioligand Competition Binding

Human embryonic kidney cells (HEK293) which express recombinant mouse NPY-Y5 receptors (mNPY-Y5) were disrupted by being frozen/thawed three times in hypotonic Tris buffer (5 mM, pH 7.4, 1 mM $MgCl_2$), after which they were homogenized and centrifuged at 72 000 G for 15 minutes. The precipitate was washed twice with Tris buffer (pH 7.4) containing 25 mM $MgCl_2$, 250 mM sucrose, 0.1 mM phenylmethylsulfonyl fluoride and 0.1 mM 1,10-phenanthroline, then resuspended in the same buffer and stored in aliquots at −80° C. The protein was determined by the Lowry method using bovine serum albumin (BSA) as the standard.

The competition binding analysis was carried out in 250 μl of 25 mM Hepes buffer (pH 7.4, 2.5 mM $CaCl_2$, 1 mM $MgCl_2$, 1% bovine serum albumin and 0.01% sodium azide) which 5 μg of protein, 100 pM $^{125}$I-labeled peptide YY (PYY) and 10 μl of a DMSO solution containing increasing quantities of DMSO solution containing unlabeled test compound. After a one-hour incubation at 22° C., the bound ligand was separated from the unbound ligand by means of filtration through a glass fiber filter. Nonspecific binding was determined in the presence of 1 μM unlabeled PYY. Specific binding is defined as the difference between total binding and nonspecific binding. An $IC_{50}$ value is defined as the concentration of the antagonist which displaces 50% of the $^{125}$I-labeled neuropeptide Y. This concentration is determined by linear regression analysis following logit/log transformation of the binding values.

In the above-described test, preferred compounds according to the invention exhibit $IC_{50}$ values of less than 1000 nM, while particularly preferred compounds exhibit $IC_{50}$ values of less than 100 nM and very particularly preferred compounds exhibit $IC_{50}$ values of less than 50 nM.

The results which were obtained in the above-described test using representative compounds of the formula I as test compounds are compiled in the following table.

| Substance | NPY5 $IC_{50}$ (μM) |
|---|---|
| rac. N-(9-Ethyl-9H-carbazol-3-yl)-5-oxo-1-(2-pyridin-2-ylethyl)pyrrolidine-3-carboxamide | 0.003 |
| rac. N-(9-Ethyl-9H-carbazol-3-yl)-1-(2-hydroxy-2-phenylethyl)-5-oxopyrrolidine-3-carboxamide | 0.008 |
| rac. N-(4-Diethylaminophenyl)-1-(2,5-dimethylphenyl)-5-oxopyrrolidine-3-carboxamide | 0.009 |
| rac. N-(9-Ethyl-9H-carbazol-3-yl)-5-oxo-1-(2-thiophen-2-ylethyl)pyrrolidine-3-carboxamide | 0.010 |
| rac. N-(9-Ethyl-9H-carbazol-3-yl)-1-(4-chlorobenzyl)-5-oxopyrrolidine-3-carboxamide | 0.010 |
| rac. N-(9-Ethyl-9H-carbazol-3-yl)-5-oxo-1-thiophen-2-ylmethylpyrrolidine-3-carboxamide | 0.010 |
| rac. N-(9-Ethyl-9H-carbazol-3-yl)-1-furan-2-ylmethyl-5-oxopyrrolidine-3-carboxamide | 0.010 |
| rac. N-(9-Ethyl-9H-carbazol-3-yl)-1-(2-isopropylphenyl)-5-oxopyrrolidine-3-carboxamide | 0.010 |
| rac. N-(9-Ethyl-9H-carbazol-3-yl)-1-(5-methoxy-2-methylphenyl)-5-oxopyrrolidine-3-carboxamide | 0.010 |
| rac. N-[4-(Ethylisopropylamino)phenyl]-1-(2,5-dimethylphenyl)-5-oxopyrrolidine-3-carboxamide | 0.010 |
| rac. N-(9-Ethyl-9H-carbazol-3-yl)-5-oxo-1-phenethylpyrrolidine-3-carboxamide | 0.012 |
| rac. Ethyl [(4-{[1-(2,5-dimethylphenyl)-5-oxopyrrolidine-3-carbonyl]amino}phenyl)phenylamino]acetate | 0.013 |
| rac. N-(9-Ethyl-9H-carbazol-3-yl)-1-cycloheptyl-5-oxopyrrolidine-3-carboxamide | 0.015 |
| rac. N-{4-[(4,6-Dimethylpyrimidin-2-yl)ethylamino]phenyl}-1-(5-methoxy-2-methylphenyl)-5-oxopyrrolidine-3-carboxamide | 0.015 |
| rac. N-{4-[Ethyl-(2-hydroxyethyl)amino]phenyl}-1-(2,5-dimethylphenyl)-5-oxopyrrolidine-3-carboxamide | 0.016 |
| rac. N-[4-(Ethylphenylamino)phenyl]-1-(2,5-dimethylphenyl)-5-oxopyrrolidine-3-carboxamide | 0.017 |
| rac. N-(9-Ethyl-9H-carbazol-3-yl)-1-(3-methoxyphenyl)-5-oxopyrrolidine-3-carboxamide | 0.020 |
| rac. N-(9-Ethyl-9H-carbazol-3-yl)-1-(2-chlorobenzyl)-5-oxopyrrolidine-3-carboxamide | 0.020 |
| rac. N-[4-(4,6-Dimethylpyrimidin-2-ylamino)phenyl]-1-(2,5-dimethylphenyl)-5-oxopyrrolidine-3-carboxamide | 0.020 |
| rac. N-{4-[(4,6-Dimethylpyrimidin-2-yl)methylamino]phenyl}-1-(2,5-dimethylphenyl)-5-oxopyrrolidine-3-carboxamide | 0.020 |
| rac. N-(9-Ethyl-9H-carbazol-3-yl)-5-oxo-1-phenylpyrrolidine-3-carboxamide | 0.021 |
| rac. N-{4-[(4,6-Dimethylpyrimidin-2-yl)methylamino]phenyl}-5-oxo-1-p-tolylpyrrolidine-3-carboxamide | 0.022 |
| rac. N-[4-(Isopropylphenylamino)phenyl]-1-(2,5-dimethylphenyl)-5-oxopyrrolidine-3-carboxamide | 0.022 |
| rac. N-[4-(Ethylphenylamino)phenyl]-1-(2-isopropylphenyl)-5-oxopyrrolidine-3-carboxamide | 0.023 |
| rac. N-{4-[(4,6-Dimethylpyrimidin-2-yl)ethylamino]phenyl}-5-oxo-1-(2-pyridin-2-ylethyl)pyrrolidine-3-carboxamide | 0.024 |
| rac. N-[4-(4,6-Dimethylpyrimidin-2-ylamino)phenyl]-1-(2-isopropylphenyl)-5-oxopyrrolidine-3-carboxamide | 0.025 |
| rac. N-[4-(4,6-Dimethylpyrimidin-2-ylamino)phenyl]- | 0.026 |

-continued

| Substance | NPY5 IC$_{50}$ (µM) |
|---|---|
| 1-(5-methoxy-2-methylphenyl)-5-oxopyrrolidine-3-carboxamide | |
| rac. N-[4-(Methylphenylamino)phenyl]-1-(2,5-dimethylphenyl)-5-oxopyrrolidine-3-carboxamide | 0.026 |
| rac. N-[4-(Methylphenylamino)phenyl]-1-(2-isopropylphenyl)-5-oxopyrrolidine-3-carboxamide | 0.020 |
| rac. N-(9-Ethyl-9H-carbazol-3-yl)-1-(4-isopropylphenyl)-5-oxopyrrolidine-3-carboxamide | 0.030 |
| rac. N-(9-Ethyl-9H-carbazol-3-yl)-1-(3-fluoro-phenyl)-5-oxopyrrolidine-3-carboxamide | 0.030 |
| rac. N-(4-Phenylaminophenyl)-1-(2,5-dimethylphenyl)-5-oxopyrrolidine-3-carboxamide | 0.030 |
| rac. N-[4-(4,6-Dimethylpyrimidin-2-ylamino)phenyl]-1-indan-2-yl-5-oxopyrrolidine-3-carboxamide | 0.030 |
| rac. N-[4-(Ethylphenylamino)phenyl]-1-(5-methoxy-2-methylphenyl)-5-oxopyrrolidine-3-carboxamide | 0.030 |
| rac. N-{4-[(4,6-Dimethylpyrimidin-2-yl)methylamino]phenyl}-1-(2-isopropylphenyl)-5-oxopyrrolidine-3-carboxamide | 0.031 |
| rac. N-(9-Ethyl-9H-carbazol-3-yl)-1-benzyl-5-oxopyrrolidine-3-carboxamide | 0.032 |
| rac. N-[4-(4,6-Dimethylpyrimidin-2-ylamino)phenyl]-5-oxo-1-p-tolylpyrrolidine-3-carboxamide | 0.032 |
| rac. N-(9-Ethyl-9H-carbazol-3-yl)-1-indan-2-yl-5-oxopyrrolidine-3-carboxamide | 0.032 |
| rac. N-{4-[(4,6-Dimethylpyrimidin-2-yl)ethylamino]phenyl}-1-(2-hydroxy-2-phenylethyl)-5-oxo-pyrrolidine-3-carboxamide | 0.033 |
| rac. N-(Biphenyl-4-yl)-1-(2,5-dimethylphenyl)-5-oxo-pyrrolidine-3-carboxamide | 0.034 |
| rac. N-[4-(Cyclopropylmethylphenylamino)phenyl]-1-(5-methoxy-2-methylphenyl)-5-oxopyrrolidine-3-carboxamide | 0.034 |
| rac. N-[4-(Isopropylphenylamino)phenyl]-1-(2-isopropylphenyl)-5-oxopyrrolidine-3-carboxamide | 0.034 |
| rac. N-(4-Phenylaminophenyl)-1-(2-isopropylphenyl)-5-oxopyrrolidine-3-carboxamide | 0.041 |
| rac. N-{4-[(4,6-Dimethylpyrimidin-2-yl)methylamino]phenyl}-1-(5-methoxy-2-methylphenyl)-5-oxopyrrolidine-3-carboxamide | 0.041 |
| rac. N-{4-[(4,6-Dimethylpyrimidin-2-yl)ethylamino]phenyl}-1-(3-methoxyphenyl)-5-oxopyrrolidine-3-carboxamide | 0.044 |
| rac. N-(4-Isopropylphenyl)-1-(2,5-dimethylphenyl)-5-oxopyrrolidine-3-carboxamide | 0.045 |
| rac. N-[4-(Cyclopropylmethylphenylamino)phenyl]-1-(2,5-dimethylphenyl)-5-oxopyrrolidine-3-carboxamide | 0.045 |
| rac. N-{4-[(4,6-Dimethylpyrimidin-2-yl)ethylamino]phenyl}-1-(2-isopropylphenyl)-5-oxopyrrolidine-3-carboxamide | 0.046 |
| rac. Ethyl [(4-{[1-(5-methoxy-2-methylphenyl)-5-oxo-pyrrolidine-3-carbonyl]amino}phenyl)phenylamino]-acetate | 0.046 |
| rac. N-[4-(Cyclopropylmethylphenylamino)phenyl]-1-(2-isopropylphenyl)-5-oxopyrrolidine-3-carboxamide | 0.047 |
| rac. N-[4-(Ethylphenylamino)phenyl]-1-indan-2-yl-5-oxopyrrolidine-3-carboxamide; | 0.049 |
| rac. N-(9-Ethyl-9H-carbazol-3-yl)-1-(2-morpholin-4-ylethyl)-5-oxopyrrolidine-3-carboxamide | 0.01 |
| rac. N-(9-Ethyl-9H-carbazol-3-yl)-5-oxo-1-p-tolyl-pyrrolidine-3-carboxamide | 0.03 |
| rac. N-(9-Ethyl-9H-carbazol-3-yl)-1-(2,4-dimethoxybenzyl)-5-oxopyrrolidine-3-carboxamide | 0.02 |

Methods which are well known and familiar to every skilled person can be used to bring the compounds according to the invention into suitable pharmaceutical forms for administration. Examples of these administration forms are tablets, lacquered tablets, sugar-coated tablets, capsules, solutions for injection, etc. Excipients and auxiliary substances which are suitable for producing these pharmaceutical administration forms are likewise well known and familiar to every skilled person. In addition to one or more compounds according to the invention, these administration forms can also comprise additional pharmacological active compounds.

The attending physician has to adjust the dosage of the compounds according to the invention, or of the administration forms which comprise them, in dependence on the particular requirements of the patient. In general, a daily dose of 0.1–20 mg, preferably 0.5–5 mg, of a compound according to the invention per kg of the patient's body weight ought to be appropriate.

The following examples are intended to clarify the invention without, however, restricting its scope in any way.

EXAMPLE 1

R$^1$ is Phenyl 20.5 mg (0.1 mmol) of rac. 5-oxo-1-phenylpyrrolidine-3-carboxylic acid (Buzas et al., Chim Ther 7, 398–403, 1972), dissolved in 0.5 ml of methylene chloride/DMF (9:1), were added to solid phase coupling reagents (DCC, loading 1.7 mmol/g). The mixture was shaken for 5 minutes after which 13.6 mg (0.1 mmol) of N,N-dimethyl-p-phenylenediamine, dissolved in 0.5 ml of methylene chloride/DMF (9:1), were added and the mixture was shaken at room temperature overnight. The solid was then filtered off and the filtrate was evaporated; the residue was dissolved in 1 ml of methylene chloride and methylisocyanate polystyrene (1.8 mmol/g) (solid phase scavenger) was then added to the solution, which was shaken at room temperature for 12 hours and then filtered; Tris(2-aminoethyl)amine polystyrene (3.4 mmol/g) was then added to the filtrate, which was shaken at room temperature for 12 hours and then filtered; the filtrate was evaporated. This resulted in 18 mg of colorless rac. N-(4-dimethylaminophenyl)-5-oxo-1-phenylpyrrolidine-3-carboxamide, MS (M+H) 324.3, MS (M–H) 322.5.

EXAMPLE 2

R$^1$ is Phenyl

The following products were prepared in analogy with example 1 and using the amines which are listed below:
a) from 4-phenoxyaniline, rac. N-(4-phenoxyphenyl)-5-oxo-1-phenylpyrrolidine-3-carboxamide, MS(M+H) 373.3, MS(M–H) 371.4.
b) from 2-(3,4-dimethoxyphenyl)ethylamine, rac. N-[2-(3,4-dimethoxyphenyl)ethyl]-5-oxo-1-phenylpyrrolidine-3-carboxamide, MS(M+H) 369.3.
c) from N-(4-aminophenyl)-N-ethyl-4,6-dimethyl-2-pyrimidine, rac. N-{4-[(4,6-dimethylpyrimidin-2-yl)ethylamino]phenyl}-5-oxo-1-phenylpyrrolidine-3-carboxamide, MS(M+H) 430.3, MS(M–H) 428.5.
d) from 2-aminofluorene, rac. N-(9H-fluoren-2-yl)-5-oxo-1-phenylpyrrolidine-3-carboxamide, MS(M+H9) 369.3, MS(M–H) 367.4.
e) from 3-aminobiphenyl, rac. N-(biphenyl-3-yl)-5-oxo-1-phenylpyrrolidine-3-carboxamide, MS(M+H) 357.2, MS(M–H) 355.4.
f) from N-(4-aminophenyl)-4,6-dimethyl-2-pyrimidineamine, N-[4-(4,6-dimethylpyrimidin-2-ylamino)phenyl]-5-oxo-1-phenylpyrrolidine-3-carboxamide, MS(M+H) 402.3, MS(M–H) 400.5.
g) from N-(4-aminophenyl)-N-methyl-4,6-dimethyl-2-pyrimidine, rac. N-{4-[(4,6-dimethylpyrimidin-2-yl)methylamino]phenyl}-5-oxo-1-phenylpyrrolidine-3-carboxamide, MS(M+H) 416.3, MS(M–H) 414.5.

h) from N-phenyl-1,4-phenylenediamine, rac. N-(4-phenylaminophenyl)-5-oxo-1-phenylpyrrolidine-3-carboxamide, MS(M+H) 372.2, MS(M–H) 370.5.

i) from 3-amino-9-ethylcarbazole, rac. N-(9-ethyl-9H-carbazol-3-yl)-5-oxo-1-phenylpyrrolidine-3-carboxamide, MS(M+H) 398.2, MS(M–H) 396.3.

EXAMPLE 3

$R^1$ is Benzyl a) The following products were prepared from rac. 1-benzyl-5-oxo-1-pyrrolidine-3-carboxylic acid, in analogy with example 1, using the amines which are listed below:

a1) from N-(4-aminophenyl)-N-ethyl-4,6-dimethyl-2-pyrimidine, rac. N-{4-[(4,6-dimethylpyrimidin-2-yl)ethylamino]phenyl}-1-benzyl-5-oxopyrrolidine-3-carboxamide, MS(M+H) 444.3, MS(M–H) 442.5.

a2) from N-(4-aminophenyl)-N-methyl-4,6-dimethyl-2-pyrimidine, rac. N-{4-[(4,6-dimethylpyrimidin-2-yl)methylamino]phenyl}-1-benzyl-5-oxopyrrolidine-3-carboxamide, MS(M+H) 430.4, MS(M–H) 428.5.

a3) from 3-amino-9-ethylcarbazole, rac. N-(9-ethyl-9H-carbazol-3-yl)-1-benzyl-5-oxopyrrolidine-3-carboxamide, MS(M+H) 412.1, MS(M–H) 410.3.

b) The rac. 1-benzyl-5-oxo-1-pyrrolidine-3-carboxylic acid which was required for example 3a was prepared from benzylamine and itaconic acid in analogy with a protocol published by Buzas et al. (Chim Ther 7, 398–403 (1972)).

EXAMPLE 4

$R^1$ is 2,5-dimethylphenyl a) The following products were prepared from rac. 1-(2,5-dimethylphenyl)-5-oxo-1-pyrrolidine-3-carboxylic acid, in analogy with example 1, using the amines which are listed below:

a1) from 4'-aminoacetophenone, rac. N-(4-acetylphenyl)-1-(2,5-dimethylphenyl)-5-oxopyrrolidine-3-carboxamide, MS(M+H) 351.3, MS(M–H) 349.5.

a2) from 3-aminobiphenyl, rac. N-(biphenyl-3-yl)-1-(2,5-dimethylphenyl)-5-oxopyrrolidine-3-carboxamide, MS(M+H) 385.3, MS(M–H) 383.4.

a3) from 3-amino-2-methoxydibenzofuran, rac. N-(2-methoxydibenzofuran-3-yl)-1-(2,5-dimethylphenyl)-5-oxopyrrolidine-3-carboxamide, MS(M+H) 429.2, MS(M–H) 427.4.

a4) from 2-amino-9-fluorenone, rac. N-(9-oxo-9H-fluoren-2-yl)-1-(2,5-dimethylphenyl)-5-oxopyrrolidine-3-carboxamide, MS(M+H) 411.2, MS(M–H) 409.4.

a5) from 2-aminofluorene, rac. N-(9H-fluoren-2-yl)-1-(2,5-dimethylphenyl)-5-oxopyrrlidine-3-carboxamide, MS(M+H) 397.3, MS(M–H) 395.5.

a6) from N-(4-aminophenyl)-N-ethyl-4,6-dimethyl-2-pyrimidine, rac. N-{4-[(4,6-dimethylpyrimidin-2-yl)ethylamino]phenyl}-1-(2,5-dimethylphenyl)-5-oxopyrrolidine-3-carboxamide, MS(M+H) 458.4, MS(M–H) 456.5.

a7) from N-(4-aminophenyl)-4,6-dimethyl-2-pyrimidineamine, rac. N-[4-(4,6-dimethylpyrimidin-2-ylamino)phenyl]-1-(2,5-dimethylphenyl)-5-oxopyrrolidine-3-carboxamide, MS(M+H) 430.4, MS(M–H) 428.5.

a8) from N-(4-aminophenyl)-N-methyl-4,6-dimethyl-2-pyrimidine, rac. N-{4-[(4,6-dimethylpyrimidin-2-yl)methylamino]phenyl}-1-(2,5-dimethylphenyl)-5-oxopyrrolidine-3-carboxamide, MS(M+H) 444.4, MS(M–H) 442.5.

a9) from N-phenyl-1,4-phenylenediamine, rac. N-(4-phenylaminophenyl)-1-(2,5-dimethylphenyl)-5-oxopyrrolidine-3-carboxamide, MS(M+H) 400.3, MS(M–H) 398.5.

a10) from N,N-dimethyl-p-phenylenediamine, rac. N-(4-dimethylaminophenyl)-1-(2,5-dimethylphenyl)-5-oxopyrrolidine-3-carboxamide, MS(M+H) 352.3, MS(M–H) 350.5.

a11) from p-methoxyaniline, rac. N-(4-methoxyphenyl)-1-(2,5-dimethylphenyl)-5-oxopyrrolidine-3-carboxamide, MS(M+H) 339.2, MS(M–H) 337.4.

a12) from N-ethyl-N-(2-hydroxyethyl)-p-phenylenediamine, rac. N-{4-[ethyl-(2-hydroxyethyl)amino]phenyl}-1-(2,5-dimethylphenyl)-5-oxopyrrolidine-3-carboxamide, MS(M+H) 396.4, MS(M–H) 394.5.

a13) from 4-amino-N-ethyl-N-isopropylaniline, rac. N-[4-(ethylisopropylamino)phenyl]-1-(2,5-dimethylphenyl)-5-oxopyrrolidine-3-carboxamide, MS(M+H) 394.4, MS(M–H) 392.5.

a14) from 4-amino-N,N-diethylaniline, rac. N-(4-diethylaminophenyl)-1-(2,5-dimethylphenyl)-5-oxopyrrolidine-3-carboxamide, MS(M+H) 380.4, MS(M–H) 378.5.

a15) from 1-amino-9-fluorene, rac. N-(9H-fluoren-1-yl)-1-(2,5-dimethylphenyl)-5-oxopyrrolidine-3-carboxamide, MS(M+H) 397.3, MS(M–H) 395.5.

a16) from 4-aminobiphenyl, rac. N-(biphenyl-4-yl)-1-(2,5-dimethylphenyl)-5-oxopyrrolidine-3-carboxamide, MS(M+H) 385.3, MS(M–H) 383.4.

a17) from ethyl [(4-aminophenyl)phenylamino]acetate (example 4b2), rac. ethyl [(4-{[1-(2,5-dimethylphenyl)-5-oxopyrrolidine-3-carbonyl]amino}phenyl)phenylamino]acetate, MS(M+H) 486.4, MS(M–H) 484.5.

a18) from N-cyclopropylmethyl-N-phenylphenylene-1,4-diamine(example 4c2), rac. N-[4-(cyclopropylmethylphenylamino)phenyl]-1-(2,5-dimethylphenyl)-5-oxopyrrolidine-3-carboxamide, MS(M+H) 454.15, MS(M–H) 454.5.

a19) from N-isobutyl-N-phenylphenylene-1,4-diamine (example 4d2), rac. N-[4-(isobutylphenylamino)phenyl]-1-(2,5-dimethylphenyl)-5-oxopyrrolidine-3-carboxamide, MS(M+H) 456.4, MS(M–H) 454.5.

a20) from N-methyl-N-phenylphenylene-1,4-diamine (example 4e2), rac. N-[4-(methylphenylamino)phenyl]-1-(2,5-dimethylphenyl)-5-oxopyrrolidine-3-carboxamide, MS(M+H) 414.3, MS(M–H) 412.5.

a21) from ethyl [(4-aminophenyl)phenylamino]pentanoate (example 4f2), rac. ethyl 5-[(4-{[1-(2,5-dimethylphenyl)-5-oxopyrrolidine-3-carbonyl]amino}phenyl)phenylamino]pentanoate, MS(M+H) 528.5.

a22) from N-benzyl-N-phenyl-1,4-diamine(example 4g2), rac. N-[4-(benzylphenylamino)phenyl]-1-(2,5-dimethylphenyl)-5-oxopyrrolidine-3-carboxamide, MS(M+H) 490.3, MS(M–H) 488.5.

a23) from N-isopropyl-N-phenyl-1,4-diamine(example 4h2), rac. N-[4-(isopropylphenylamino)phenyl]-1-(2,5-dimethylphenyl)-5-oxopyrrolidine-3-carboxamide, MS(M+H) 442.4, MS(M–H) 440.5.

a24) from N-ethyl-N-phenyl-1,4-diamine(example 4i2), rac. N-[4-(ethylphenylamino)phenyl]-1-(2,5-dimethylphenyl)-5-oxopyrrolidine-3-carboxamide, MS(M+H) 428.4, MS(M–H) 426.5.

b) The rac. 2,5-dimethylphenyl-5-oxo-1-pyrrolidine-3-carboxylic acid which was required for example 4a was prepared in analogy with example 3b) but using 2,5-dimethylaniline in place of benzylamine.

b1) The ethyl [(4-aminophenyl)phenylamino]acetate required in example 4a17) was prepared as follows: 62 mg of sodium hydride dispersion (60%), and then 178 µl of ethyl bromoacetate, were added to a solution of 300 mg of 4-nitrodiphenylamine in 3 ml of DMF. The reaction mixture was stirred at room temperature for 16 hours and then at 50° C. for 4 hours, after which it was cooled down and diluted with 3 ml of toluene; the solution was then filtered. The filtrate was evaporated and the residue was purified by chromatography on silica gel (pentane/toluene). This resulted in 197 mg of pure ethyl [(4-nitrophenyl)phenylamino]acetate.

b2) The 197 mg of ethyl [(4-nitrophenyl)phenylamino]acetate which were obtained as described in example 4b1 were dissolved in 2 ml of methanol after which 20 mg of palladium/charcoal catalyst were added and the mixture was hydrogenated at room temperature for 3 hours. After the reaction mixture had been filtered and the filtrate evaporated, 173 mg of ethyl [(4-aminophenyl)phenylamino]acetate, MS(M+H) 271.1, were obtained.

c1) The cyclopropylmethyl(4-nitrophenyl)phenylamine was prepared in analogy with example 4b1 but using (bromomethyl)cyclopropane in place of ethyl bromoacetate.

c2) The N-cyclopropylmethyl-N-phenylphenylene-1,4-diamine, MS(M+H) 239.3, was prepared in analogy with example 4b2 but using the product from example 4c1.

d1) The isobutyl(4-nitrophenyl)phenylamine was prepared in analogy with example 4b1 but using 3-bromo-2-methylpropane in place of ethyl bromoacetate.

d2) The N-isobutyl-N-phenylphenylene-1,4-diamine, MS(M+H) 241.3, was prepared in analogy with example 4b2 but using the product from example 4d1.

e1) The methyl(4-nitrophenyl)phenylamine was prepared in analogy with example 4b1 but using methyl iodide in place of ethyl bromoacetate.

e2) The N-methyl-N-phenylphenylene-1,4-diamine, MS(M+H) 199.3, was prepared in analogy with example 4b2 but using the product from example 4e1.

f1) The ethyl [(4-nitrophenyl)phenylamino]pentanoate was prepared in analogy with example 4b1 but using ethyl bromopentanoate in place of ethyl bromoacetate.

f2) The ethyl [(4-aminophenyl)phenylamino]pentanoate, MS(M+H) 313.2, was prepared in analogy with example 4b2 but using the product from example 4f1.

g1) The benzyl(4-nitrophenyl)phenylamine was prepared in analogy with example 4b1 but using benzyl bromide in place of ethyl bromoacetate.

g2) The N-benzyl-N-phenylphenylene-1,4-diamine, MS(M+H) 275.3, was prepared in analogy with example 4b2 but using the product from example 4g1.

h1) The isopropyl(4-nitrophenyl)phenylamine was prepared in analogy with example 4b1 but using 2-bromopropane in place of ethyl bromoacetate.

h2) The N-isopropyl-N-phenylphenylene-1,4-diamine, MS(M+H) 227.3, was prepared in analogy with example 4b2 but using the product from example 4h1.

i1) The ethyl(4-nitrophenyl)phenylamine was prepared in analogy with example 4b1 but using bromoethane in place of ethyl bromoacetate.

i2) The N-ethyl-N-phenylphenylene-1,4-diamine, MS(M+H) 213.3, was prepared in analogy with example 4b2 but using the product from example 4i1.

EXAMPLE 5

$R^1$ is Indan-2-yl a) The following products were prepared from rac. 1-indan-2-yl-5-oxopyrrolidine-3-carboxylic cid, in analogy with example 1, using the amines which are listed below:

a1) from 3-aminobiphenyl, rac. N-(biphenyl-3-yl)-1-indan-2-yl-5-oxopyrrolidine-3-carboxamide, MS(M+H) 397.3, MS(M−H) 395.5.

a2) from 3-amino-2-methoxydibenzofuran, rac. N-(2-methoxydibenzofuran-3-yl)-1-indan-2-yl-5-oxopyrrolidine-3-carboxamide, MS(M+H) 441.2, MS(M−H) 439.5.

a3) from 2-amino-9-fluorenone, rac. N-(9-oxo-9H-fluoren-2-yl)-1-indan-2-yl-5-oxopyrrolidine-3-carboxamide, MS(M+H) 423.2, MS(M−H) 421.4.

a4) from 2-aminofluorene, rac. N-(9H-fluoren-2-yl)-1-indan-2-yl-5-oxopyrrolidine-3-carboxamide, MS(M+H) 409.3, MS(M−H) 407.5.

a5) from N-(4-aminophenyl)-N-ethyl-4,6-dimethyl-2-pyrimidine, rac. N-{4-[(4,6-dimethylpyrimidin-2-yl)ethylamino]phenyl}-1-indan-2-yl-5-oxopyrrolidine-3-carboxamide, MS(M+H) 470.4, MS(M−H) 468.5.

a6) from N-(4-aminophenyl)-4,6-dimethyl-2-pyrimidineamine, rac. N-[4-(4,6-dimethylpyrimidin-2-ylamino)phenyl]-1-indan-2-yl-5-oxopyrrolidine-3-carboxamide, MS(M+H) 442.4, MS(M−H) 440.5.

a7) from N-(4-aminophenyl)-N-methyl-4,6-dimethyl-2-pyrimidine, rac. N-{4-[(4,6-dimethylpyrimidin-2-yl)methylamino]phenyl}-1-indan-2-yl-5-oxopyrrolidine-3-carboxamide, MS(M+H) 456.3, MS(M−H) 454.5.

a8) from N-phenyl-1,4-phenylenediamine, rac. N-(4-phenylaminophenyl)-1-indan-2-yl-5-oxopyrrolidine-3-carboxamide, MS(M+H) 412.3, MS(M−H) 410.5.

a9) from 1-amino-9-fluorene, rac. N-(9H-fluoren-1-yl)-1-indan-2-yl-5-oxopyrrolidine-3-carboxamide, MS(M+H) 409.3, MS(M−H) 407.5.

a10) from 4-aminobiphenyl, rac. N-(biphenyl-4-yl)-1-indan-2-yl-5-oxopyrrolidine-3-carboxamide, MS(M+H) 397.3, MS(M−H) 395.5.

a11) from 3-amino-9-ethylcarbazole, rac. N-(9-ethyl-9H-carbazol-3-yl)-1-indan-2-yl-5-oxopyrrolidine-3-carboxamide, MS(M+H) 438.4, MS(M−H) 436.3.

a12) from N,N-dimethyl-p-phenylenediamine, rac. N-(4-dimethylaminophenyl)-1-indan-2-yl-5-oxopyrrolidine-3-carboxamide, MS(M+H) 364.3, MS(M−H) 362.1.

a13) from ethyl [(4-aminophenyl)phenylamino]acetate (see example 3a22), rac. ethyl({4-[(1-indan-2-yl-5-oxopyrrolidine-3-carbonyl)amino]phenyl}phenylamino)acetate, MS(M+H) 498.3, MS(M−H) 496.5.

a14) from N-cyclopropylmethyl-N-phenylphenylene-1,4-diamine (see example 3a23), rac. N-[4-(cyclopropylmethylphenylamino)phenyl]-1-indan-2-yl-5-oxopyrrolidine-3-carboxamide, MS(M+H) 466.4, MS(M−H) 464.5.

a15) from N-isobutyl-N-phenylphenylene-1,4-diamine (example 4d2), rac. N-[4-(isobutylphenylamino)phenyl]-1-indan-2-yl-5-oxopyrrolidine-3-carboxamide, MS(M+H) 468.3, MS(M−H) 466.5.

a16) from N-methyl-N-phenylphenylene-1,4-diamine (example 4e2), rac. N-[4-(methylphenylamino)phenyl]-1-indan-2-yl-5-oxopyrrolidine-3-carboxamide, MS(M+H) 426.3, MS(M−H) 424.5.

a17) from ethyl [(4-aminophenyl)phenylamino]pentanoate (example 4f2), rac. ethyl 5-({4-[(1-indan-2-yl-5-oxopyrrolidine-3-carbonyl)amino]phenyl}phenylamino)pentanoate, MS(M+H) 540.4, MS(M−H) 538.5.

a18) from N-benzyl-N-phenylphenylene-1,4-diamine (example 4g2), rac. N-[4-(benzylphenylamino)phenyl]-1-indan-2-yl-5-oxopyrrolidine-3-carboxamide, MS(M+H) 502.3, MS(M−H) 500.5.

a19) from N-isopropyl-N-phenylphenylene-1,4-diamine (example 4h2), rac. N-[4-(isopropylphenylamino)phenyl]-1-indan-2-yl-5-oxopyrrolidine-3-carboxamide, MS(M+H) 454.4, MS(M−H) 452.5.

a20) from N-ethyl-N-phenylphenylene-1,4-diamine (example 4i2), rac. N-[4-(ethylphenylamino)phenyl]-1-indan-2-yl-5-oxopyrrolidine-3-carboxamide, MS(M+H) 440.3, MS(M−H) 438.5.

b) The rac. 1-indan-2-yl-5-oxopyrrolidine-3-carboxylic acid required for example 5a was prepared in analogy with example 3b) but using indan-2-amine in place of benzylamine.

EXAMPLE 6

$R^1$ is 2-naphthyl a) The following products were prepared from rac. 1-naphthalen-2-yl-5-oxopyrrolidine-3-carboxylic acid, in analogy with example 1, using the amines which are listed below:

a1) from 4-phenoxyaniline, rac. N-(4-phenoxyphenyl)-1-naphthalen-2-yl-5-oxopyrrolidine-3-carboxamide, MS(M+H) 423.4, MS(M−H) 421.3.

a2) from N,N-dimethyl-p-phenylenediamine, rac. N-(4-dimethylaminophenyl)-1-naphthalen-2-yl-5-oxopyrrolidine-3-carboxamide, MS(M+H) 374.3, MS(M−H) 372.5.

b) The rac. 1-naphthalen-2-yl-5-oxopyrrolidine-3-carboxylic acid required for example 6a was prepared in analogy with example 3b) but using 2-naphthylamine in place of benzylamine.

EXAMPLE 7

$R^1$ is 2-isopropylphenyl a) The following products were prepared from rac. 1-(2-isopropylphenyl)-5-oxopyrrolidine-3-carboxylic acid, in analogy with example 1, using the amines which are listed below:

a1) from N-(4-aminophenyl)-4,6-dimethyl-2-pyrimidineamine, rac. N-[4-(4,6-dimethylpyrimidin-2-ylamino)phenyl]-1-(2-isopropylphenyl)-5-oxopyrrolidine-3-carboxamide, MS(M+H) 444.4, MS(M−H) 442.5.

a2) from N-(4-aminophenyl)-N-methyl-4,6-dimethyl-2-pyrimidine, rac. N-{4-[(4,6-dimethylpyrimidin-2-yl)methylamino]phenyl}-1-(2-isopropylphenyl)-5-oxopyrrolidine-3-carboxamide, MS(M+H) 458.4, MS(M−H) 456.5.

a3) from N-(4-aminophenyl)-N-ethyl-4,6-dimethyl-2-pyrimidine, rac. N-{4-[(4,6-dimethylpyrimidin-2-yl)ethylamino]phenyl}-1-(2-isopropylphenyl)-5-oxopyrrolidine-3-carboxamide, MS(M+H) 472.2, MS(M−H) 470.5.

a4) from N-phenyl-1,4-phenylenediamine, rac. N-(4-phenylaminophenyl)-1-(2-isopropylphenyl)-5-oxopyrrolidine-3-carboxamide, MS(M+H) 414.3, MS(M−H) 412.5.

a5) from 3-amino-9-ethylcarbazole, rac. N-(9-ethyl-9H-carbazol-3-yl)-1-(2-isopropylphenyl)-5-oxopyrrolidine-3-carboxamide, MS(M+H) 440'.4, MS(M−H) 438.3.

a6) from ethyl [(4-aminophenyl)phenylamino]acetate (see example 3a22), rac. ethyl [(4-{[1-(2-isopropylphenyl)-5-oxopyrrolidine-3-carbonyl]amino}phenyl)phenylamino]acetate, MS(M+H) 500.3, MS(M−H) 498.5.

a7) from N-cyclopropylmethyl-N-phenylphenylene-1,4-diamine (see example 3a23), rac. N-[4-(cyclopropylmethylphenylamino)phenyl]-1-(2-isopropylphenyl)-5-oxopyrrolidine-3-carboxamide, MS(M+H) 468.4, MS(M−H) 466.5.

a8) from N-isobutyl-N-phenylphenylene-1,4-diamine (example 4d2), rac. N-[4-(isobutylphenylamino)phenyl]-1-(2-isopropylphenyl)-5-oxopyrrolidine-3-carboxamide, MS(M+H) 470.4, MS(M−H) 468.5.

a9) from N-methyl-N-phenylphenylene-1,4-diamine (example 4e2), rac. N-[4-(methylphenylamino)phenyl]-1-(2-isopropylphenyl)-5-oxopyrrolidine-3-carboxamide, MS(M+H) 428.4, MS(M−H) 426.5.

a10) from ethyl [(4-aminophenyl)phenylamino]pentanoate (example 4f2), rac. ethyl 5-[(4-{([1-(2-isopropylphenyl)-5-oxopyrrolidine-3-carbonyl]amino}phenyl)phenylamino]pentanoate, MS(M+H) 542.4, MS(M−H) 540.6.

a11) from N-benzyl-N-phenylphenylene-1,4-diamine (example 4g2), rac. N-[4-(benzylphenylamino)phenyl]-1-(2-isopropylphenyl)-5-oxopyrrolidine-3-carboxamide, MS(M+H) 504.3, MS(M−H) 502.5.

a12) from N-isopropyl-N-phenylphenylene-1,4-diamine (example 4h2), rac. N-[4-(isopropylphenylamino)phenyl]-1-(2-isopropylphenyl)-5-oxopyrrolidine-3-carboxamide, MS(M+H) 456.4, MS(M−H) 454.5.

a13) from N-ethyl-N-phenylphenylene-1,4-diamine (example 4i2), rac. N-[4-(ethylphenylamino)phenyl]1-(2-isopropylphenyl)-5-oxopyrrolidine-3-carboxamide, MS(M+H) 442.4, MS(M−H) 440.5.

b) The rac. 1-(2-isopropylphenyl)-5-oxopyrrolidine-3-carboxylic acid required for example 7a was prepared in analogy with example 3b) but using isopropylamine in place of benzylamine.

EXAMPLE 8

$R^1$ is 2-phenylethyl a) The following products were prepared from rac. 5-oxo-1-phenethylpyrrolidine-3-carboxylic acid, in analogy with example 1, using the amines which are listed below:

a1) from 4-phenoxyaniline, rac. N-(4-phenoxyphenyl)-5-oxo-1-phenethylpyrrolidine-3-carboxamide, MS(M+H) 401.3, MS(M−H) 399.5.

a2) from N,N-dimethyl-p-phenylenediamine, rac. N-(4-dimethylaminophenyl)-5-oxo-1-phenethylpyrrolidine-3-carboxamide, MS(M+H) 352.3, MS(M−H) 350.5.

a3) from N-(4-aminophenyl)-N-ethyl-4,6-dimethyl-2-pyrimidine, rac. N-{4-[(4,6-dimethylpyrimidin-2-yl)ethylamino]phenyl}-5-oxo-1-phenethylpyrrolidine-3-carboxamide, MS(M+H) 458.4, MS(M−H) 456.5.

a4) from 3-aminobiphenyl, rac. N-(biphenyl-3-yl)-5-oxo-1-phenethylpyrrolidine-3-carboxamide, MS(M+H) 385.2, MS(M−H) 383.4.

a5) from 2-amino-9-fluorenone, rac. N-(9-oxo-9H-fluoren-2-yl)-5-oxo-1-phenethylpyrrolidine-3-carboxamide, MS(M+H) 411.3, MS(M−H) 409.4.

a6) from 2-aminofluorene, rac. N-(9H-fluoren-2-yl)-5-oxo-1-phenethylpyrrolidine-3-carboxamide, MS(M+H) 397.3, MS(M−H) 395.5.

a7) from N-(4-aminophenyl)-4,6-dimethyl-2-pyrimidineamine, rac. N-[4-(4,6-dimethylpyrimidin-2-ylamino)phenyl]-5-oxo-1-phenethylpyrrolidine-3-carboxamide, MS(M+H) 430.3, MS(M−H) 428.5.

a8) from N-(4-aminophenyl)-N-methyl-4,6-dimethyl-2-pyrimidine, rac. N-{4-[(4,6-dimethylpyrimidin-2-yl)methylamino]phenyl}-5-oxo-1-phenethylpyrrolidine-3-carboxamide, MS(M+H) 444.3, MS(M−H) 442.5.

a9) from N-phenyl-1,4-phenylenediamine, rac. N-(4-phenylaminophenyl)-5-oxo-1-phenethylpyrrolidine-3-carboxamide, MS(M+H) 400.3, MS(M−H) 398.5.

a10) from 4-aminobiphenyl, rac. N-(biphenyl-4-yl)-5-oxo-1-phenethylpyrrolidine-3-carboxamide, MS(M+) 385.4, MS(M−H) 383.4.

a11) from 3-amino-9-ethylcarbazole, rac. N-(9-ethyl-9H-carbazol-3-yl)-5-oxo-1-phenethylpyrrolidine-3-carboxamide, MS(M+H) 426.3, MS(M–H) 424.4.

b) The rac. 5-oxo-1-phenethylpyrrolidine-3-carboxylic acid required for example 8a was prepared in analogy with example 3b) but using phenethylamine in place of benzylamine.

EXAMPLE 9

$R^1$ is 5-methoxy-2-methylphenyl a) The following compounds were prepared from rac. 1-(5-methoxy-2-methylphenyl)-5-oxopyrrolidine-3-carboxylic acid, in analogy with example 1, using the amines which are listed below:

a1) from N-(4-aminophenyl)-4,6-dimethyl-2-pyrimidineamine, rac. N-[4-(4,6-dimethylpyrimidin-2-ylamino)phenyl]-1-(5-methoxy-2-methylphenyl)-5-oxopyrrolidine-3-carboxamide, MS(M+H) 446.4, MS(M–H) 444.5.

a2) from N-(4-aminophenyl)-N-methyl-4,6-dimethyl-2-pyrimidine, rac. N-{4-[(4,6-dimethylpyrimidin-2-yl)methylamino]phenyl}-1-(5-methoxy-2-methylphenyl)-5-oxopyrrolidine-3-carboxamide, MS(M+H) 460.4, MS(M–H) 458.5.

a3) from N-(4-aminophenyl)-N-ethyl-4,6-dimethyl-2-pyrimidine, rac. N-{4-[(4,6-dimethylpyrimidin-2-yl)ethylamino]phenyl}-1-(5-methoxy-2-methylphenyl)-5-oxopyrrolidine-3-carboxamide, MS(M+H) 474.0, MS(M–H) 472.5.

a4) from N-phenyl-1,4-phenylenediamine, rac. N-(4-phenylaminophenyl)-1-(5-methoxy-2-methylphenyl)-5-oxopyrrolidine-3-carboxamide, MS(M+H) 416.3, MS(M–H) 414.5.

a5) from 3-amino-9-ethylcarbazole, rac. N-(9-ethyl-9H-carbazol-3-yl)-1-(5-methoxy-2-methylphenyl)-5-oxopyrrolidine-3-carboxamide, MS(M+H) 442.6, MS(M–H) 440.3.

a6) from ethyl [(4-aminophenyl)phenylamino]acetate (see example 3a22), rac. ethyl [(4-{[1-(5-methoxy-2-methylphenyl)-5-oxopyrrolidine-3-carbonyl]amino}phenyl)phenylamino]acetate, MS(M+H) 502.3, MS(M–H) 500.5.

a7) from N-cyclopropylmethyl-N-phenylphenylene-1,4-diamine (see example 3a23), rac. N-[4-(cyclopropylmethylphenylamino)phenyl]-1-(5-methoxy-2-methylphenyl)-5-oxopyrrolidine-3-carboxamide, MS(M+H) 470.4, MS(M–H) 468.5.

a8) from N-isobutyl-N-phenylphenylene-1,4-diamine (example 4d2), rac. N-[4-(isobutylphenylamino)phenyl]-1-(5-methoxy-2-methylphenyl-5-oxopyrrolidine-3-carboxamide, MS(M+H) 472.3, MS(M–H) 470.5.

a9) from N-methyl-N-phenylphenylene-1,4-diamine (example 4e2), rac. N-[4-(methylphenylamino)phenyl]-1-(5-methoxy-2-methylphenyl)-5-oxopyrrolidine-3-carboxamide, MS(M+H) 430.3, MS(M–H) 428.5.

a10) from ethyl [(4-aminophenyl)phenylamino]pentanoate (example 4f2), rac. ethyl 5-[(4-{[1-(5-methoxy-2-methylphenyl)-5-oxopyrrolidine-3-carbonyl]amino}phenyl)phenylamino]pentanoate, MS(M+H) 544.5, MS(M–H) 542.6.

a11) from N-benzyl-N-phenylphenylene-1,4-diamine (example 4g2), rac. N-[4-(benzylphenylamino)phenyl]-1-(5-methoxy-2-methylphenyl)-5-oxopyrrolidine-3-carboxamide, MS(M+H) 506.3, MS(M–H) 504.5.

a12) from N-isopropyl-N-phenylphenylene-1,4-diamine (example 4h2), rac. N-[4-(isopropylphenylamino)phenyl]-1-(5-methoxy-2-methylphenyl)-5-oxopyrrolidine-3-carboxamide, MS(M+H) 458.4, MS(M–H) 456.5.

a13) from N-ethyl-N-phenylphenylene-1,4-diamine (example 4i2); rac. N-[4-(ethylphenylamino)phenyl]-1-(5-methoxy-2-methylphenyl)-5-oxopyrrolidine-3-carboxamide, MS(M+H) 444.4, MS(M–H) 442.5.

b) The rac. 1-(5-methoxy-2-methylphenyl)-5-oxopyrrolidine-3-carboxylic acid required for example 9a was prepared in analogy with example 3b) but using 5-methoxy-2-methylaniline in place of benzylamine.

EXAMPLE 10

$R^1$ is Morpholinoethyl a) The following products were prepared from rac. 1-(2-morpholin-4-ylethyl)-5-oxopyrrolidine-3-carboxylic acid, in analogy with example 1, using the amines which are listed below:

a1) from 2-aminofluorene, rac. N-(9H-fluoren-2-yl)-1-(2-morpholin-4-ylethyl)-5-oxopyrrolidine-3-carboxamide, MS(M+H) 406.4, MS(M–H) 404.5.

a2) from N-(4-aminophenyl)-N-ethyl-4,6-dimethyl-2-pyrimidine, rac. N-{4-[(4,6-dimethylpyrimidin-2-yl)ethylamino]phenyl}-1-(2-morpholin-4-ylethyl)-5-oxopyrrolidine-3-carboxamide, MS(M+H) 467.3, MS(M–H) 4465.5.

a3) from 3-amino-9-ethylcarbazole, rac. N-(9-ethyl-9H-carbazol-3-yl)-1-(2-morpholin-4-ylethyl)-5-oxopyrrolidine-3-carboxamide, MS(M+H) 435.5, MS(M–H) 433.3.

b) The rac. 1-(5-methoxy-2-methylphenyl)-5-oxopyrrolidine-3-carboxylic acid required for example 10a was prepared in analogy with example 3b) but using 4-(2-aminoethyl)morpholine in place of benzylamine.

EXAMPLE 11

$R^1$ is thien-2-ylethyl a) The following products were prepared from rac. 5-oxo-1-(2-thiophen-2-ylethyl)pyrrolidine-3-carboxylic acid, in analogy with example 1, using the amines which are listed below:

a1) from N-(4-aminophenyl)-4,6-dimethyl-2-pyrimidineamine, rac. N-[4-(4,6-dimethylpyrimidin-2-ylamino)phenyl]-5-oxo-1-(2-thiophen-2-ylethyl)pyrrolidine-3-carboxamide, MS(M+H) 436.3, MS(M–H) 434.5.

a2) from N-(4-aminophenyl)-N-methyl-4,6-dimethyl-2-pyrimidine, rac. N-{4-[(4,6-dimethylpyrimidin-2-yl)methylamino]phenyl}-5-oxo-1-(2-thiophen-2-ylethyl)pyrrolidine-3-carboxamide, MS(M+H) 450.3, MS(M–H) 448.4.

a3) from N-(4-aminophenyl)-N-ethyl-4,6-dimethyl-2-pyrimidine, rac. N-{4-[(4,6-dimethylpyrimidin-2-yl)ethylamino]phenyl}-5-oxo-1-(2-thiophen-2-ylethyl)pyrrolidine-3-carboxamide, MS(M+H) 464.5, MS(M–H) 462.5.

a4) from N-phenyl-1,4-phenylenediamine, rac. N-(4-phenylaminophenyl)-5-oxo-1-(2-thiophen-2-ylethyl)pyrrolidine-3-carboxamide, MS(M+H) 406.2, MS(M–H) 404.4.

a5) from 3-amino-9-ethylcarbazole, rac. N-(9-ethyl-9H-carbazol-3-yl)-5-oxo-1-(2-thiophen-2-ylethyl)pyrrolidine-3-carboxamide, MS(M+H) 432.2, MS(M–H) 430.2.

b) The rac. 5-oxo-1-(2-thiophen-2-ylethyl)pyrrolidine-3-carboxylic acid required for example 11a was prepared in analogy with example 3b) but using 2-thiophene-ethylamine in place of benzylamine.

EXAMPLE 12

$R^1$ is 2-pyridin-2-ylethyl a) The following products were prepared from rac. 5-oxo-1-(2-pyridin-2-ylethyl)pyrrolidine-3-carboxylic acid, in analogy with example 1, using the amines which are listed below:
a1) from N-(4-aminophenyl)-4,6-dimethyl-2-pyrimidineamine, rac. N-[4-(4,6-dimethylpyrimidin-2-ylamino)phenyl]-5-oxo-1-(2-pyridin-2-ylethyl)pyrrolidine-3-carboxamide, MS(M+H) 431.3, MS(M–H) 429.5.
a2) from N-(4-aminophenyl)-N-methyl-4,6-dimethyl-2-pyrimidine, rac. N-{4-[(4,6-dimethylpyrimidin-2-yl)methylamino]phenyl}-5-oxo-1-(2-pyridin-2-ylethyl)pyrrolidine-3-carboxamide, MS(M+H) 445.3, MS(M–H) 443.5.
a3) from N-(4-aminophenyl)-N-ethyl-4,6-dimethyl-2-pyrimidine, rac. N-{4-[(4,6-dimethylpyrimidin-2-yl)ethylamino]phenyl}-5-oxo-1-(2-pyridin-2-ylethyl)pyrrolidine-3-carboxamide, MS(M+H) 459.3, MS(M–H) 457.5.
a4) from N-phenyl-1,4-phenylenediamine, rac. N-(4-phenylaminophenyl)-5-oxo-1-(2-pyridin-2-ylethyl)pyrrolidine-3-carboxamide, MS(M+H) 401.3, MS(M–H) 399.5.
a5) from 3-amino-9-ethylcarbazole, rac. N-(9-ethyl-9H-carbazol-3-yl)-5-oxo-1-(2-pyridin-2-ylethyl)pyrrolidine-3-carboxamide, MS(M+H) 427.5, MS(M–H) 425.4.
b) The rac. 5-oxo-1-(2-pyridin-2-ylethyl)pyrrolidine-3-carboxylic acid required for example 12a was prepared in analogy with example 3b) but using 2-(2-aminoethyl)pyridine in place of benzylamine.

EXAMPLE 13

$R^1$ is p-tolyl a) The following products were prepared from rac. 5-oxo-1-p-tolylpyrrolidine-3-carboxylic acid, in analogy with example 1, using the amines which are listed below:
a1) from N-(4-aminophenyl)-4,6-dimethyl-2-pyrimidineamine, rac. N-[4-(4,6-dimethylpyrimidin-2-ylamino)phenyl]-5-oxo-1-p-tolylpyrrolidine-3-carboxamide, MS(M+H) 416.4, MS(M–H) 414.5.
a2) from N-(4-aminophenyl)-N-methyl-4,6-dimethyl-2-pyrimidine, rac. N-{4-[(4,6-dimethylpyrimidin-2-yl)methylamino]phenyl}-5-oxo-1-p-tolylpyrrolidine-3-carboxamide, MS(M+H) 430.4, MS(M–H) 428.4.
a3) from N-(4-aminophenyl)-N-ethyl-4,6-dimethyl-2-pyrimidine, rac. N-{4-[(4,6-dimethylpyrimidin-2-yl)ethylamino]phenyl}-5-oxo-1-p-tolylpyrrolidine-3-carboxamide, MS(M+H) 444.3, MS(M–H) 442.5.
a4) from N-phenyl-1,4-phenylenediamine, rac. N-(4-phenylaminophenyl)-5-oxo-1-p-tolylpyrrolidine-3-carboxamide, MS(M+H) 386.3, MS(M–H) 384.4.
a5) from 3-amino-9-ethylcarbazole, rac. N-(9-ethyl-9H-carbazol-3-yl)-5-oxo-1-p-tolylpyrrolidine-3-carboxamide, MS(M+H) 412.1, MS(M–H) 410.3.
b) The rac. 5-oxo-1-p-tolylpyrrolidine-3-carboxylic acid required for example 13a was prepared in analogy with example 3b) but using p-toluidine in place of benzylamine.

EXAMPLE 14

$R^1$ is m-methoxyphenyl a) The following products were prepared from rac. 1-(3-methoxyphenyl)-5-oxopyrrolidine-3-carboxylic acid, in analogy with example 1, using the amines which are listed below:
a1) from N-(4-aminophenyl)-4,6-dimethyl-2-pyrimidineamine, rac. N-[4-(4,6-dimethylpyrimidin-2-ylamino)phenyl]-1-(3-methoxyphenyl)-5-oxopyrrolidine-3-carboxamide, MS(M+H) 432.2, MS(M–H) 430.5.
a2) from N-(4-aminophenyl)-N-methyl-4,6-dimethyl-2-pyrimidine, rac. N-{4-[(4,6-dimethylpyrimidin-2-yl)methylamino]phenyl}-1-(3-methoxyphenyl)-5-oxopyrrolidine-3-carboxamide, MS(M+H) 446.4, MS(M–H) 444.5.
a3) from N-(4-aminophenyl)-N-ethyl-4,6-dimethyl-2-pyrimidine, rac. N-{4-[(4,6-dimethylpyrimidin-2-yl)ethylamino]phenyl}-1-(3-methoxyphenyl)-5-oxopyrrolidine-3-carboxamide, MS(M+H) 460.3, MS(M–H) 458.5.
a4) from N-phenyl-1,4-phenylenediamine, rac. N-(4-phenylaminophenyl)-1-(3-methoxyphenyl)-5-oxopyrrolidine-3-carboxamide, MS(M+H) 402.2, MS(M–H) 400.4.
a5) from 3-amino-9-ethylcarbazole, rac. N-(9-ethyl-9H-carbazol-3-yl)-1-(3-methoxyphenyl)-5-oxopyrrolidine-3-carboxamide, MS(M+H) 428.2, MS(M–H) 426.3.
b) The rac. 1-(3-methoxyphenyl)-5-oxopyrrolidine-3-carboxylic acid required for example 14a was prepared in analogy with example 3b) but using m-anisidine in place of benzylamine.

EXAMPLE 15

$R^1$ is Cycloheptyl a) The following products were prepared from rac. 1-cycloheptyl-5-oxopyrrolidine-3-carboxylic acid, in analogy with example 1, using the amines which are listed below:
a1) from N-(4-aminophenyl)-4,6-dimethyl-2-pyrimidineamine, rac. N-[4-(4,6-dimethylpyrimidin-2-ylamino)phenyl]-1-cycloheptyl-5-oxopyrrolidine-3-carboxamide, MS(M+H) 422.5, MS(M–H) 420.5.
a2) from N-(4-aminophenyl)-N-methyl-4,6-dimethyl-2-pyrimidine, rac. N-{4-[(4,6-dimethylpyrimidin-2-yl)methylamino]phenyl}-1-cycloheptyl-5-oxopyrrolidine-3-carboxamide, MS(M+H) 436.6, MS(M–H) 434.0.
a3) from N-(4-aminophenyl)-N-ethyl-4,6-dimethyl-2-pyrimidine, rac. N-{4-[(4,6-dimethylpyrimidin-2-yl)ethylamino]phenyl}-1-cycloheptyl-5-oxopyrrolidine-3-carboxamide, MS(M+H) 450.6, MS(M–H) 448.6.
a4) from N-phenyl-1,4-phenylenediamine, rac. N-(4-phenylaminophenyl)-1-cycloheptyl-5-oxopyrrolidine-3-carboxamide, MS(M+H) 392.4, MS(M–H) 390.5.
a5) from 3-amino-9-ethylcarbazole, rac. N-(9-ethyl-9H-carbazol-3-yl)-1-cycloheptyl-5-oxopyrrolidine-3-carboxamide, MS(M+H) 418.5, MS(M–H) 426.3.
b) The rac. 1-cycloheptyl-5-oxopyrrolidine-3-carboxylic acid required for example 15a was prepared in analogy with example 3b) but using cycloheptylamine in place of benzylamine; MS(M+H) 226.1, MS(M–H) 224.1.

EXAMPLE 16

$R^1$ is naphthalen-1-ylmethyl a) The following products were prepared from rac. 1-naphthalen-1-ylmethyl-5-oxopyrrolidine-3-carboxylic acid, in analogy with example 1, using the amines which are listed below:

a1) from N-(4-aminophenyl)-4,6-dimethyl-2-pyrimidineamine, rac. N-[4-(4,6-dimethylpyrimidin-2-ylamino)phenyl]-1-naphthalen-1-ylmethyl-5-oxopyrrolidine-3-carboxamide, MS(M+H) 466.3, MS(M–H) 464.3.

a2) from N-(4-aminophenyl)-N-methyl-4,6-dimethyl-2-pyrimidine, rac. N-{4-[(4,6-dimethylpyrimidin-2-yl)methylamino]phenyl}-1-naphthalen-1-ylmethyl-5-oxopyrrolidine-3-carboxamide, MS(M+H) 480.4, MS(M–H) 478.5 a3) from N-(4-aminophenyl)-N-ethyl-4,6-dimethyl-2-pyrimidine, rac. N-{4-[(4,6-dimethylpyrimidin-2-yl)ethylamino]phenyl}-1-naphthalen-1-ylmethyl-5-oxopyrrolidine-3-carboxamide, MS(M+H) 494.4, MS(M–H) 492.5.

b) The rac. 1-naphthalen-1-ylmethyl-5-oxopyrrolidine-3-carboxylic acid required for example 16a was prepared in analogy with example 3b) but using 1-naphlyl-methylamine in place of benzylamine; MS(M+H) 270.1, MS(M–H) 268.1.

EXAMPLE 18

$R^1$ is 2-hydroxy-2-phenylethyl a) The following products were prepared from rac. 1-(2-hydroxy-2-phenylethyl)-5-oxopyrrolidine-3-carboxylic acid, in analogy with example 1, using the amines which are listed below:

a1) from N-(4-aminophenyl)-4,6-dimethyl-2-pyrimidineamine, rac. N-[4-(4,6-dimethylpyrimidin-2-ylamino)phenyl]-1-(2-hydroxy-2-phenylethyl)-5-oxopyrrolidine-3-carboxamide, MS(M+H) 446.4, MS(M–H) 444.5.

a2) from N-(4-aminophenyl)-N-methyl-4,6-dimethyl-2-pyrimidine, rac. N-{4-[(4,6-dimethylpyrimidin-2-yl)methylamino]phenyl}-1-(2-hydroxy-2-phenylethyl)-5-oxopyrrolidine-3-carboxamide, MS(M+H) 460.6, MS(M–H) 458.5.

a3) from N-(4-aminophenyl)-N-ethyl-4,6-dimethyl-2-pyrimidine, rac. N-{4-[(4,6-dimethylpyrimidin-2-yl)ethylamino]phenyl}-1-(2-hydroxy-2-phenylethyl)-5-oxopyrrolidine-3-carboxamide, MS(M+H) 475.6, MS(M–H) 472.5.

a4) from N-phenyl-1,4-phenylenediamine, rac. N-(4-phenylaminophenyl)-1-(2-hydroxy-2-phenylethyl)-5-oxopyrrolidine-3-carboxamide, MS(M+H) 416.3, MS(M–H) 414.5.

a5) from 3-amino-9-ethylcarbazole, rac. N-(9-ethyl-9H-carbazol-3-yl)-1-(2-hydroxy-2-phenylethyl)-5-oxopyrrolidine-3-carboxamide, MS(M+H) 442.6, MS(M–H) 440.3.

b) The rac. 1-(2-hydroxy-2-phenylethyl)-5-oxopyrrolidine-3-carboxylic acid required for example 18a was prepared in analogy with example 3b) but using 2-hydroxy-2-phenylethylamine in place of benzylamine; MS(M+H) 250.1, MS(M–H) 248.1.

EXAMPLE 18

$R^1$ is m-tolyl a) The following products were prepared from rac. 5-oxo-1-m-tolylpyrrolidine-3-carboxylic acid, in analogy with example 1, using the amines which are listed below:

a1) from N-(4-aminophenyl)-4,6-dimethyl-2-pyrimidineamine, rac. N-[4-(4,6-dimethylpyrimidin-2-ylamino)phenyl]-5-oxo-1-m-tolylpyrrolidine-3-carboxamide, MS(M+H) 416.3, MS(M–H) 414.5.

a2) from N-(4-aminophenyl)-N-methyl-4,6-dimethyl-2-pyrimidine, rac. N-{4-[(4,6-dimethylpyrimidin-2-yl)methylamino]phenyl}-5-oxo-1-m-tolylpyrrolidine-3-carboxamide, MS(M+H) 430, MS(M–H) 428.5.

a3) from N-(4-aminophenyl)-N-ethyl-4,6-dimethyl-2-pyrimidine, rac. N-{4-[(4,6-dimethylpyrimidin-2-yl)ethylamino]phenyl}-5-oxo-1-m-tolylpyrrolidine-3-carboxamide, MS(M+H) 444.6, MS(M–H) 442.5.

a4) from N-phenyl-1,4-phenylenediamine, rac. N-(4-phenylaminophenyl)-5-oxo-1-N-tolylpyrrolidine-3-carboxamide, MS(M+H) 386.3, MS(M–H) 384.5.

b) The rac. 5-oxo-1-m-tolylpyrrolidine-3-carboxylic acid required for example 18a was prepared in analogy with example 3b) but using m-toluidine in place of benzylamine; MS(M+H) 220.1, MS(M–H) 218.1.

EXAMPLE 19

$R^1$ is 2-thienylmethyl a) The following product was prepared from rac. 5-oxo-1-(2-thienylmethyl)pyrrolidine-3-carboxylic acid (Maybridge), in analogy with example 1, using the amine which is listed below:

a1) from 3-amino-9-ethylcarbazole, rac. N-(9-ethyl-9H-carbazol-3-yl)-5-oxo-1-thiophen-2-ylmethylpyrrolidine-3-carboxamide, MS(M+H) 418.1, MS(M–H) 416.2.

EXAMPLE 20

$R^1$ is 2-furylmethyl a) The following products were prepared from rac. 1-(2-furylmethyl)-5-oxopyrrolidine-3-carboxylic acid (Maybridge), in analogy with example 1 using the amines which are listed below:

a1) from N-(4-aminophenyl)-4,6-dimethyl-2-pyrimidineamine, rac. N-[4-(4,6-dimethylpyrimidin-2-ylamino)phenyl]-1-furan-2-ylmethyl-5-oxopyrrolidine-3-carboxamide, MS(M+H) 406.3, MS(M–H) 404.5.

a2) from N-(4-aminophenyl)-N-methyl-4,6-dimethyl-2-pyrimidine, rac. N-{4-[(4,6-dimethylpyrimidin-2-yl)methylamino]phenyl}-1-furan-2-ylmethyl-5-oxopyrrolidine-3-carboxamide, MS(M+H) 420.5, MS(M–H) 418.5.

a3) from N-(4-aminophenyl)-N-ethyl-4,6-dimethyl-2-pyrimidine, rac. N-{4-[4,6-dimethylpyrimidin-2-yl)ethylamino]phenyl}-1-furan-2-ylmethyl-5-oxopyrrolidine-3-carboxamide, MS(M+H) 434.6, MS(M–H) 432.5.

a4) from N-phenyl-1,4-phenylenediamine, rac. N-(4-phenylaminophenyl)-1-furan-2-ylmethyl-5-oxopyrrolidine-3-carboxamide, MS(M+H) 376.3, MS(M–H) 474.5.

a5) from 3-amino-9-ethylcarbazole, rac. N-(9-ethyl-9H-carbazol-3-yl)-1-furan-2-ylmethyl-5-oxopyrrolidine-3-carboxamide, MS(M+H) 401.9, MS(M–H) 400.1.

EXAMPLE 21

R¹ is p-chlorobenzyl a) The following product was prepared from rac. 1-(4-chlorobenzyl)-5-oxopyrrolidine-3-carboxylic acid (Maybridge), in analogy with example 1, using the amine which is listed below:
a1) from 3-amino-9-ethylcarbazole, rac. N-(9-ethyl-9H-carbazol-3-yl)-1-(4-chlorobenzyl)-5-oxopyrrolidine-3-carboxamide, MS(M+H) 446.1, MS(M−H) 444.1.

EXAMPLE 22

R¹ is p-dimethylaminophenyl a) In analogy with example 1, and using suitable amines, rac. 1-(4-dimethylaminophenyl)-5-oxopyrrolidine-3-carboxylic acid can be converted into products of the formula I.
a1) from N-(4-aminophenyl)-4,6-dimethyl-2-pyrimidineamine, rac. N-[4-(4,6-dimethylpyrimidin-2-ylamino)phenyl]-1-(4-dimethylaminophenyl)-5-oxopyrrolidine-3-carboxamide, MS(M+H) 445.2, MS(M−H) 443.5.
a2) from N-(4-aminophenyl)-N-methyl-4,6-dimethyl-2-pyrimidineamine, rac. N-{4-[(4,6-dimethylpyrimidin-2-yl)methylamino]phenyl}-1-(4-dimethylaminophenyl)-5-oxopyrrolidine-3-carboxamide, MS(M+H) 459.4, MS(M−H) 457.5.
b) The rac. 1-(4-dimethylaminophenyl)-5-oxopyrrolidine-3-carboxylic acid required for example 22a was prepared in analogy with example 3b but using N,N-dimethyl-p-phenylenediamine in place of benzylamine; MS(M+H) 249.1, MS(M−H) 247.1.

EXAMPLE 23

R¹ is 2-pyrrolidin-1-ylethyl a) The following product was prepared from rac. 5-oxo-1-(2-pyrrolidin-1-ylethyl)pyrrolidine-3-carboxylic acid, in analogy with example 1, using the amine which is listed below:
a1) from N-(4-aminophenyl)-N-ethyl-4,6-dimethyl-2-pyrimidine, rac. N-{4-[(4,6-dimethylpyrimidin-2-yl)ethylamino]phenyl}-5-oxo-1-(2-pyrrolidin-1-ylethyl)pyrrolidine-3-carboxamide, MS(M+H) 451.2, MS(M−H) 449.3.
b) The rac. 5-oxo-1-(2-pyrrolidin-1-ylethyl)pyrrolidine-3-carboxylic acid required for example 23a was prepared in analogy with example 3b but using 1-(2-aminoethyl)pyrrolidine in place of benzylamine; MS(M+H) 227.1, MS(M−H) 225.1.

EXAMPLE 24

R¹ is 1-methylpyrrolidin-2-ylethyl a) The following product was prepared from rac. 1-[2-(1-methylpyrrolidin-2-yl)ethyl]-5-oxopyrrolidine-3-carboxylic acid, in analogy with example 1, using the amine which is listed below:
a1) from 3-amino-9-ethylcarbazole, rac. N-(9-ethyl-9H-carbazol-3-yl)-1-[2-(1-methylpyrrolidin-2-yl)ethyl]-5-oxopyrrolidine-3-carboxamide, MS(M+H) 433.4, MS(M−H) 431.3.
b) The rac. 1-[2-(1-methylpyrrolidin-2-yl)ethyl]-5-oxopyrrolidine-3-carboxylic acid required for example 24a was prepared in analogy with example 3b) but using 2-(2-aminoethyl)-1-methylpyrrolidine in place of benzylamine; MS(M+H) 241.2, MS(M−H) 239.1.

EXAMPLE 25

R¹ is 4-isopropylphenyl a) The following product was prepared from rac. 1-(4-isopropylphenyl)-5-oxopyrrolidine-3-carboxylic acid, in analogy with example 1, using the amine which is listed below:
a1) from 3-amino-9-ethylcarbazole, rac. N-(9-ethyl-9H-carbazol-3-yl)-1-(4-isopropylphenyl)-5-oxopyrrolidine-3-carboxamide, MS(M+H) 440.4, MS(M−H) 438.3.
b) The rac. 1-(4-isopropylphenyl)-5-oxopyrrolidine-3-carboxylic acid required for example 25a was prepared in analogy with example 3b) but using 4-isopropylaniline in place of benzylamine; MS(M+H) 248.1, MS(M−H) 246.1.

EXAMPLE 26

R¹ is 3,5-bis-(trifluoromethyl)-phenyl a) The following product was prepared from rac. 1-(3,5-bis-(trifluoromethyl)-phenyl)-5-oxopyrrolidine-3-carboxylic acid, in analogy with example 1, using the amine which is listed below:
a1) from 3-amino-9-ethylcarbazole, rac. N-(9-ethyl-9H-carbazol-3-yl)-1-(3,5-bistrifluoromethylphenyl)-5-oxopyrrolidine-3-carboxamide, MS(M+H) 534.4.
§
b) The rac. 1-(3,5-bistrifluoromethylphenyl)-5-oxopyrrolidine-3-carboxylic acid required for example 26a was prepared in analogy with example 3b) but using 3,5-bis(trifluoromethyl)aniline in place of benzylamine.

EXAMPLE 27

R¹ is 3-fluorophenyl a) The following product was prepared from rac. 1-(3-fluorophenyl)-5-oxopyrrolidine-3-carboxylic acid, in analogy with example 1, using the amine which is listed below:
a1) from 3-amino-9-ethylcarbazole, rac. N-(9-ethyl-9H-carbazol-3-yl)-1-(3-fluorophenyl)-5-oxopyrrolidine-3-carboxamide, MS(M+H) 416.1, MS(M−H) 414.2.
b) The rac. 1-(3-fluorophenyl)-5-oxopyrrolidine-3-carboxylic acid required for example 27a was prepared in analogy with example 3b) but using 3-fluoroaniline in place of benzylamine; MS(M+H) 224.2, MS(M−H) 222.1.

EXAMPLE 28

R¹ is 2-chlorobenzyl a) The following product was prepared from rac. 1-(2-chlorobenzyl)-5-oxopyrrolidine-3-carboxylic acid, in analogy with example 1, using the amine which is listed below:
a1) from 3-amino-9-ethylcarbazole, rac. N-(9-ethyl-9H-carbazol-3-yl)-1-(2-chlorobenzyl)-5-oxopyrrolidine-3-carboxamide, MS(M+H) 446.2, MS(M−H) 444.2.
b) The rac. 1-(2-chlorobenzyl)-5-oxopyrrolidine-3-carboxylic acid required for example 28a was prepared in analogy with example 3b) but using 2-chlorobenzylamine in place of benzylamine; MS(M+H) 254.1, MS(M−H) 252.1.

EXAMPLE 29

Enantiomerically Pure Compounds

The rac. N-(9-ethyl-9H-carbazol-3-yl)-1-(2-isopropylphenyl)-5-oxopyrrolidine-3-carboxamide prepared as described in example 7a5) can be resolved into the two enantiomers
(a) (R)-N-(9-ethyl-9H-carbazol-3-yl)-1-(2-isopropylphenyl)-5-oxopyrrolidine-3-carboxamide; and
(b) (S)-N-(9-ethyl-9H-carbazol-3-yl)-1-(2-isopropylphenyl)-5-oxopyrrolidine-3-carboxamide by means of HPLC on a LichroCART (R,R) Whelk-01 column using a solvent gradient (n-hexane+0.5% acetic acid/isopropanol+0.5% acetic acid).

EXAMPLE 30

Enantiomerically Pure Compounds

The following racemic compounds can be resolved into the corresponding enantiomers in analogy with example 29:
rac. N-(9-Ethyl-9H-carbazol-3-yl)-5-oxo-1-(2-pyridin-2-ylethyl)pyrrolidine-3-carboxamide;
rac. N-(9-Ethyl-9H-carbazol-3-yl)-1-(2-hydroxy-2-phenylethyl)-5-oxopyrrolidine-3-carboxamide;
rac. N-(4-Diethylaminophenyl)-1-(2,5-dimethylphenyl)-5-oxopyrrolidine-3-carboxamide;
rac. N-(9-Ethyl-9H-carbazol-3-yl)-5-oxo-1-(2-thiophen-2-ylethyl)pyrrolidine-3-carboxamide;
rac. N-(9-Ethyl-9H-carbazol-3-yl)-1-(4-chlorobenzyl)-5-oxopyrrolidine-3-carboxamide;
rac. N-(9-Ethyl-9H-carbazol-3-yl)-5-oxo-1-thiophen-2-ylmethylpyrrolidine-3-carboxamide;
rac. N-(9-Ethyl-9H-carbazol-3-yl)-1-furan-2-ylmethyl-5-oxopyrrolidine-3-carboxamide;
rac. N-(9-Ethyl-9H-carbazol-3-yl)-1-(5-methoxy-2-methylphenyl)-5-oxopyrrolidine-3-carboxamide;
rac. N-[4-(Ethylisopropylamino)phenyl]-1-(2,5-dimethylphenyl)-5-oxopyrrolidine-3-carboxamide;
rac. N-(9-Ethyl-9H-carbazol-3-yl)-5-oxo-1-phenethylpyrrolidine-3-carboxamide;
rac. Ethyl [(4-{[1-(2,5-dimethylphenyl)-5-oxopyrrolidine-3-carbonyl]amino}phenyl)phenylamino]acetate;
rac. N-(9-Ethyl-9H-carbazol-3-yl)-1-cycloheptyl-5-oxopyrrolidine-3-carboxamide;
rac. N-{4-[(4,6-Dimethylpyrimidin-2-yl)ethylamino]phenyl}-1-(5-methoxy-2-methylphenyl)-5-oxopyrrolidine-3-carboxamide;
rac. N-{4-[Ethyl-(2-hydroxyethyl)amino]phenyl}-1-(2,5-dimethylphenyl)-5-oxopyrrolidine-3-carboxamide;
rac. N-[4-(Ethylphenylamino)phenyl]-1-(2,5-dimethylphenyl)-5-oxopyrrolidine-3-carboxamide;
rac. N-(9-Ethyl-9H-carbazol-3-yl)-1-(3-methoxyphenyl)-5-oxopyrrolidine-3-carboxamide;
rac. N-(9-Ethyl-9H-carbazol-3-yl)-1-(2-chlorobenzyl)-5-oxopyrrolidine-3-carboxamide;
rac. N-[4-(4,6-Dimethylpyrimidin-2-ylamino)phenyl]-1-(2,5-dimethylphenyl)-5-oxopyrrolidine-3-carboxamide;
rac. N-{4-[(4,6-Dimethylpyrimidin-2-yl)methylamino]phenyl}-1-(2,5-dimethylphenyl)-5-oxopyrrolidine-3-carboxamide;
rac. N-(9-Ethyl-9H-carbazol-3-yl)-5-oxo-1-phenyl-pyrrolidine-3-carboxamide;
rac. N-{4-[(4,6-Dimethylpyrimidin-2-yl)methylamino]phenyl}-5-oxo-1-p-tolylpyrrolidine-3-carboxamide;
rac. N-[4-(Isopropylphenylamino)phenyl]-1-(2,5-dimethylphenyl)-5-oxopyrrolidine-3-carboxamide;
rac. N-[4-(Ethylphenylamino)phenyl]-1-(2-isopropylphenyl)-5-oxopyrrolidine-3-carboxamide;
rac. N-{4-[(4,6-Dimethylpyrimidin-2-yl)ethylamino]phenyl}-5-oxo-1-(2-pyridin-2-ylethyl)pyrrolidine-3-carboxamide;
rac. N-[4-(4,6-Dimethylpyrimidin-2-ylamino)phenyl]-1-(2-isopropylphenyl)-5-oxopyrrolidine-3-carboxamide;
rac. N-[4-(4,6-Dimethylpyrimidin-2-ylamino)phenyl]-1-(5-methoxy-2-methylphenyl)-5-oxopyrrolidine-3-carboxamide;
rac. N-[4-(Methylphenylamino)phenyl]-1-(2,5-dimethylphenyl)-5-oxopyrrolidine-3-carboxamide;
rac. N-[4-(Methylphenylamino)phenyl]-1-(2-isopropylphenyl)-5-oxopyrrolidine-3-carboxamide;
rac. N-(9-Ethyl-9H-carbazol-3-yl)-1-(4-isopropylphenyl)-5-oxopyrrolidine-3-carboxamide;
rac. N-(9-Ethyl-9H-carbazol-3-yl)-1-(3-fluorophenyl)-5-oxopyrrolidine-3-carboxamide;
rac. N-(4-Phenylaminophenyl)-1-(2,5-dimethylphenyl)-5-oxopyrrolidine-3-carboxamide;
rac. N-[4-(4,6-Dimethylpyrimidin-2-ylamino)phenyl]-1-indan-2-yl-5-oxopyrrolidine-3-carboxamide;
rac. N-[4-(Ethylphenylamino)phenyl]-1-(5-methoxy-2-methylphenyl)-5-oxopyrrolidine-3-carboxamide;
rac. N-{4-[(4,6-Dimethylpyrimidin-2-yl)methylamino]phenyl}-1-(2-isopropylphenyl)-5-oxopyrrolidine-3-carboxamide;
rac. N-(9-Ethyl-9H-carbazol-3-yl)-1-benzyl-5-oxopyrrolidine-3-carboxamide;
rac. N-[4-(4,6-Dimethylpyrimidin-2-ylamino)phenyl]-5-oxo-1-p-tolylpyrrolidine-3-carboxamide;
rac. N-(9-Ethyl-9H-carbazol-3-yl)-1-indan-2-yl-5-oxopyrrolidine-3-carboxamide;
rac. N-{4-[(4,6-Dimethylpyrimidin-2-yl)ethylamino]phenyl}-1-(2-hydroxy-2-phenylethyl)-5-oxo-pyrrolidine-3-carboxamide;
rac. N-(Biphenyl-4-yl)-1-(2,5-dimethylphenyl)-5-oxo-pyrrolidine-3-carboxamide;
rac. N-[4-(Cyclopropylmethylphenylamino)phenyl]-1-(5-methoxy-2-methylphenyl)-5-oxopyrrolidine-3-carboxamide;
rac. N-[4-(Isopropylphenylamino)phenyl]-1-(2-isopropylphenyl)-5-oxopyrrolidine-3-carboxamide;
rac. N-(4-Phenylaminophenyl)-1-(2-isopropylphenyl)-5-oxopyrrolidine-3-carboxamide;
rac. N-{4-[(4,6-Dimethylpyrimidin-2-yl)methylamino]phenyl}-1-(5-methoxy-2-methylphenyl)-5-oxopyrrolidine-3-carboxamide;
rac. N-{4-[(4,6-Dimethylpyrimidin-2-yl)ethylamino]phenyl}-1-(3-methoxyphenyl)-5-oxopyrrolidine-3-carboxamide;
rac. N-{4-[(4,6-Dimethylpyrimidin-2-yl)methylamino]phenyl}-5-oxo-1-m-tolylpyrrolidine-3-carboxamide;
rac. N-[4-(Cyclopropylmethylphenylamino)phenyl]-1-(2,5-dimethylphenyl)-5-oxopyrrolidine-3-carboxamide;
rac. N-{4-[(4,6-Dimethylpyrimidin-2-yl)ethylamino]phenyl}-1-(2-isopropylphenyl)-5-oxopyrrolidine-3-carboxamide;
rac. Ethyl [(4-{[1-(5-methoxy-2-methylphenyl)-5-oxopyrrolidine-3-carbonyl]amino}phenyl)phenylamino]acetate;
rac. N-[4-(Cyclopropylmethylphenylamino)phenyl]-1-(2-isopropylphenyl)-5-oxopyrrolidine-3-carboxamide; and
rac. N-[4-(Ethylphenylamino)phenyl]-1-indan-2-yl-5-oxopyrrolidine-3-carboxamide.

EXAMPLE 31

$R^1$ is 2,5-dimethylphenyl a) 29 μl of Hünig's base and 1 equivalent of the acid chloride listed below were added to a solution of 50 mg of rac. N-(4-aminophenyl)-1-(2,5-dimethylphenyl)-5-oxopyrrolidine-3-carboxamide in 0.5 ml of methylene chloride. The reaction mixture was stirred overnight at room temperature and then evaporated and the residue was chromatographed on silica gel using ethyl acetate/ethanol (8:2). The evaporated product fractions in each case yielded approx. 30 mg of product. This method was used to prepare the following compounds:

a1) with acetyl chloride, rac. N-(4-acetylaminophenyl)-1-(2,5-dimethylphenyl)-5-oxopyrrolidine-3-carboxamide, MS(M+H) 366.3, MS(M−H) 364.4.

a2) with isovaleryl chloride, rac. N-[4-(3-methylbutyrylamino)phenyl]-1-(2,5-dimethylphenyl)-5-oxopyrrolidine-3-carboxamide, MS(M+H) 408.3, MS(M−H) 406.4.

a3) with cyclopropylcarbonyl chloride, rac. N-[4-(cyclopropanecarbonylamino)phenyl]-1-(2,5-dimethylphenyl)-5-oxopyrrolidine-3-carboxamide, MS(M+H) 392.3, MS(M−H) 390.4.

a4) with benzoyl chloride, rac. N-(4-benzoylaminophenyl)-1-(2,5-dimethylphenyl)-5-oxopyrrolidine-3-carboxamide, MS(M+H) 428.3, MS(M−H) 426.4.

a5) with phenylacetyl chloride, rac. N-(4-phenylacetylaminophenyl)-1-(2,5-dimethylphenyl)-5-oxopyrrolidine-3-carboxamide, MS(M+H) 442.4, MS(M−H) 440.5.

a6) with 2-methoxybenzoyl chloride, rac. N-[4-(2-methoxybenzoylamino)phenyl]-1-(2,5-dimethylphenyl)-5-oxopyrrolidine-3-carboxamide, MS(M+H) 458.2, MS(M−H) 456.5.

a7) with piperonyloyl chloride, rac. N-{4-[(benzo-[1,3]dioxole-5-carbonyl)amino]phenyl}-1-(2,5-dimethylphenyl)-5-oxopyrrolidine-3-carboxamide, MS(M+H) 472.3, MS(M−H) 470.5.

a8) with pivaloyl chloride, rac. N-[4-(2,2-dimethylpropionylamino)phenyl]-1-(2,5-dimethylphenyl)-5-oxopyrrolidine-3-carboxamide, MS(M+H) 408.3, MS(M−H) 406.4.

a9) with 4-methoxybenzoyl chloride, rac. N-[4-(4-methoxybenzoylamino)phenyl]-1-(2,5-dimethylphenyl)-5-oxopyrrolidine-3-carboxamide, MS(M+H) 458.2, MS(M−H) 456.4.

a10) with 3-fluorobenzoyl chloride, rac. N-[4-(3-fluorobenzoylamino)phenyl]-1-(2,5-dimethylphenyl)-5-oxopyrrolidine-3-carboxamide, MS(M+H) 446.3, MS(M−H) 444.4.

a11) with 2-furoyl chloride, rac. N-{4-[(furan-2-carbonyl)amino]phenyl}-1-(2,5-dimethylphenyl)-5-oxopyrrolidine-3-carboxamide, MS(M+H) 418.4, MS(M−H) 416.4.

b) The rac. N-(4-aminophenyl)-1-(2,5-dimethylphenyl)-5-oxopyrrolidine-3-carboxamide required in example 31a) was prepared as follows:

b1) 1.18 g of p-nitroaniline, 1.95 g of N-(3-dimethylaminopropyl)-N'-ethylcarbodiimide hydrochloride (EDC HCl), 2.22 ml of Hünig's base and 1.04 g of 4-(N,N-dimethylamino)pyridine were added consecutively to a solution of 2 g of 1-(2,5-dimethylphenyl)-5-oxo-1-pyrrolidine-3-carboxylic acid (example 4b) in 28 ml of methylene chloride. The reaction mixture was stirred at 40° C. for 3 hours and then taken up in ethyl acetate and washed with water until neutral. The organic phase was evaporated and this resulted in 2.5 g of rac. N-(4-nitrophenyl)-1-(2,5-dimethylphenyl)-5-oxopyrrolidine-3-carboxamide, MS(M+H) 354.1, MS(M−H) 352.3.

b2) The 2.5 g of rac. N-(4-nitrophenyl)-1-(2,5-dimethylphenyl)-5-oxopyrrolidine-3-carboxamide which were obtained as described in example 31b1) were dissolved in 70 ml of methanol and 70 ml of methylene chloride after which 0.5 g of palladium/charcoal catalyst was added and the mixture was hydrogenated overnight at room temperature. After the reaction mixture had been filtered and the filtrate evaporated, 2.3 g of rac. N-(4-aminophenyl)-1-(2,5-dimethylphenyl)-5-oxopyrrolidine-3-carboxamide, MS(M+H) 324.3, MS(M−H) 322.4, were obtained.

EXAMPLE 32

Enantiomerically Pure Compounds

The following racemic compounds can be resolved into the corresponding enantiomers in analogy with example 29:

rac. N-(4-Acetylaminophenyl)-1-(2,5-dimethylphenyl)-5-oxopyrrolidine-3-carboxamide;

rac. N-[4-(3-Methylbutyrylamino)phenyl]-1-(2,5-dimethylphenyl)-5-oxopyrrolidine-3-carboxamide;

rac. N-[4-(Cyclopropanecarbonylamino)phenyl]-1-(2,5-dimethylphenyl)-5-oxopyrrolidine-3-carboxamide;

rac. N-(4-Benzoylaminophenyl)-1-(2,5-dimethylphenyl)-5-oxopyrrolidine-3-carboxamide;

rac. N-(4-Phenylacetylaminophenyl)-1-(2,5-dimethylphenyl)-5-oxopyrrolidine-3-carboxamide;

rac. N-[4-(2-Methoxybenzoylamino)phenyl]-1-(2,5-dimethylphenyl)-5-oxopyrrolidine-3-carboxamide;

rac. N-{4-[(Benzo[1,3]dioxole-5-carbonyl)amino]-1-(2,5-dimethylphenyl)-5-oxopyrrolidine-3-carboxamide;

rac. N-[4-(2,2-Dimethylpropionylamino)phenyl]-1-(2,5-dimethylphenyl)-5-oxopyrrolidine-3-carboxamide;

rac. N-[4-(4-Methoxybenzoylamino)phenyl]-1-(2,5-dimethylphenyl)-5-oxopyrrolidine-3-carboxamide;

rac. N-[4-(3-Fluorobenzoylamino)phenyl]-1-(2,5-dimethylphenyl)-5-oxopyrrolidine-3-carboxamide;

rac. N-{4-[(Furan-2-carbonyl)amino]phenyl}-1-(2,5-dimethylphenyl)-5-oxopyrrolidine-3-carboxamide;

rac. N-(9-Ethyl-9H-carbazol-3-yl)-1-(2-morpholin-4-ylethyl)-5-oxopyrrolidine-3-carboxamide;

rac. N-(9-Ethyl-9H-carbazol-3-yl)-5-oxo-1-p-tolylpyrrolidine-3-carboxamide; and rac. N-(9-Ethyl-9H-carbazol-3-yl)-1-(2,4-dimethoxybenzyl)-5-oxopyrrolidine-3-carboxamide.

EXAMPLE 33

Enantiomerically Pure Compounds

The following racemic compounds can be resolved into the corresponding enantiomers in analogy with example 29:

rac. N-[4-(Isobutylphenylamino)phenyl]-1-(2-isopropylphenyl)-5-oxopyrrolidine-3-carboxamide;

rac. N-[4-(4,6-Dimethylpyrimidin-2-ylamino)phenyl]-1-(4-dimethylaminophenyl)-5-oxopyrrolidine-3-carboxamide; and rac. N-[4-(4,6-Dimethylpyrimidin-2-yl)methylaminophenyl]-1-(4-dimethylaminophenyl)-5-oxopyrrolidine-3-carboxamide.

EXAMPLE 34

$R^1$ is 2,4-dimethoxybenzyl a) rac. N-(9-Ethyl-9H-carbazole-3-yl)-1-(2,4-dimethoxybenzyl)-5-oxopyrrolidine-3-carboxamide was prepared from rac. 1-(2,4-dimethoxybenzyl)-5-oxopyrrolidine-3-carboxylic acid, in analogy with example 1, using 3-amino-9-ethylcarbazole; MS(M+H) 472.4, MS(M−H) 470.2.

b) The 1-(2,4-dimethoxybenzyl)-5-oxopyrrolidine-3-carboxylic acid required for example 34a was prepared in analogy with example 3b) but using 2,4-dimethoxybenzylamine; MS(M+H) 280.1, MS(M−H) 278.1.

EXAMPLE A

A compound of the formula I can be used, in a manner known per se, as the active compound for producing tablets of the following composition:

| Per tablet | |
|---|---|
| Active compound | 200 mg |
| Microcrystalline cellulose | 155 mg |
| Corn starch | 25 mg |
| Talc | 25 mg |
| Hydroxypropylmethyl cellulose | 20 mg |
| | 425 mg |

EXAMPLE B

A compound of the formula I can be used, in a manner known per se, as the active compound for producing capsules of the following composition:

| Per capsule | |
|---|---|
| Active compound | 100 mg |
| Corn starch | 20 mg |
| Lactose | 95 mg |
| Talc | 4.5 mg |
| Magnesium stearate | 0.5 mg |
| | 220.0 mg |

What is claimed is:
1. A pyrrolidonecarboxamide of the formula

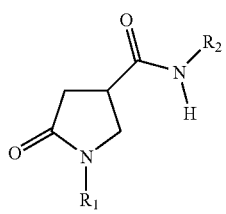

I in which
R$^1$ is phenyl which is optionally monosubstituted or disubstituted in the phenyl radical by alkyl, alkoxy, dialkylamino, halogen or trifluoromethyl; benzyl, phenylethyl or α-hydroxyphenylethyl; naphthyl or naphthylmethyl; or cycloalkyl which can optionally possess a fused-on benzene ring;
R$^2$ is a radical of the formula

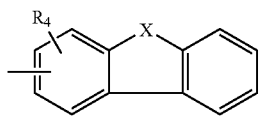

(a)

X is NR$^3$—;
R$^3$ is hydrogen or alkyl; and
R$^4$ is hydrogen or alkoxy;
pharmaceutically utilizable acid addition salts of basic compounds of the formula I, pharmaceutically utilizable salts of acid compounds of the formula I with bases, pharmaceutically utilizable esters of compounds of the formula I which contain hydroxyl or carboxyl groups, and hydrates or solvates thereof.

2. A compound as claimed in claim 1, in which R$^1$ is phenyl, 4-tolyl, 2,5-dimethylphenyl, 2-isopropylphenyl, 3-methoxyphenyl, 2-methyl-5-methoxyphenyl, benzyl, 2-phenylethyl, or 2-indanyl.

3. A compound as claimed in claim 1, in which R$^1$ is cycloheptyl, 2-hydroxy-2-phenylethyl, 4-chlorobenzyl, 3-fluorophenyl, 2,4-dimethoxybenzyl or 2-chlorobenzyl.

4. A compound as claimed in claim 1, in which R$^1$ is 2-naphthyl, naphthalen-1-ylmethyl, 4-dimethylaminophenyl, 4-isopropylphenyl or 3,5-bistrifluoromethylphenyl.

5. A compound as claimed in claim 1, in which R$^1$ is 2,5-dimethylphenyl, 2-isopropylphenyl or 2-methyl-5-methoxyphenyl.

6. A compound as claimed in claims 1, in which R$^2$ is 9-ethylcarbazol-3-yl.

7. A compound as claimed in claim 1, selected from the group consisting of:
rac. N-(9-Ethyl-9H-carbazol-3-yl)-1-(2-hydroxy-2-phenylethyl)-5-oxopyrrolidine-3-carboxamide;
rac. N-(9-Ethyl-9H-carbazol-3-yl)-1-(4-chlorobenzyl)-5-oxopyrrolidine-3-carboxamide;
rac. N-(9-Ethyl-9H-carbazol-3-yl)-1-(2-isopropylphenyl)-5-oxopyrrolidine-3-carboxamide;
rac. N-(9-Ethyl-9H-carbazol-3-yl)-1-(5-methoxy-2-methylphenyl)-5-oxopyrrolidine-3-carboxamide;
rac. N-(9-Ethyl-9H-carbazol-3-yl)-5-oxo-1-phenethylpyrrolidine-3-carboxamide;
rac. N-(9-Ethyl-9H-carbazol-3-yl)-1-cycloheptyl-5-oxopyrrolidine-3-carboxamide;
rac. N-(9-Ethyl-9H-carbazol-3-yl)-1-(3-methoxyphenyl)-5-oxopyrrolidine-3-carboxamide;
rac. N-(9-Ethyl-9H-carbazol-3-yl)-1-(2-chlorobenzyl)-5-oxopyrrolidine-3-carboxamide;
rac. N-(9-Ethyl-9H-carbazol-3-yl)-5-oxo-1-phenylpyrrolidine-3-carboxamide;
rac. N-(9-Ethyl-9H-carbazol-3-yl)-1-(4-isopropylphenyl)-5-oxopyrrolidine-3-carboxamide;
rac. N-(9-Ethyl-9H-carbazol-3-yl)-1-(3-fluorophenyl)-5-oxopyrrolidine-3-carboxamide;
rac. N-(9-Ethyl-9H-carbazol-3-yl)-1-benzyl-5-oxopyrrolidine-3-carboxamide;
rac. N-(9-Ethyl-9H-carbazol-3-yl)-1-indan-2-yl-5-oxopyrrolidine-3-carboxamide;
or a pharmaceutically acceptable salt of such a compound.

8. A compound as claimed in claim 1, selected from the group consisting of:
rac. N-(9-Ethyl-9-carbazol-3-yl)-5-oxo-1-p-tolylpyrrolidine-3-carboxamide; and
rac. N-(9-Ethyl-9H-carbazol-3-yl)-1(2,4-dimethoxybenzyl)-5-oxypyrrolidine-3-carboxamide,
or a pharmaceutically acceptable salt of such a compound.

9. A pharmaceutical composition comprising a compound as claimed in claim 1 or a pharmaceutically acceptable salt of such compound.

* * * * *